(12) United States Patent
Vatanparvar et al.

(10) Patent No.: US 12,414,696 B2
(45) Date of Patent: Sep. 16, 2025

(54) MULTIMODAL CONTACTLESS VITAL SIGN MONITORING

(71) Applicant: SAMSUNG ELECTRONICS CO., LTD., Gyeonggi-Do (KR)

(72) Inventors: Korosh Vatanparvar, Cupertino, CA (US); Wenchuan Wei, Sunnyvale, CA (US); Li Zhu, Saratoga, CA (US); Migyeong Gwak, Santa Clara, CA (US); Jilong Kuang, San Jose, CA (US); Jun Gao, Menlo Park, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 423 days.

(21) Appl. No.: 17/841,063

(22) Filed: Jun. 15, 2022

(65) Prior Publication Data
US 2023/0128766 A1 Apr. 27, 2023

Related U.S. Application Data

(60) Provisional application No. 63/272,084, filed on Oct. 26, 2021.

(51) Int. Cl.
*A61B 5/0205* (2006.01)
*G06T 7/215* (2017.01)
*G06T 7/246* (2017.01)

(52) U.S. Cl.
CPC .......... *A61B 5/0205* (2013.01); *G06T 7/215* (2017.01); *G06T 7/246* (2017.01); *G06T 2207/20182* (2013.01)

(58) Field of Classification Search
CPC ...... A61B 5/077; A61B 5/0205; A61B 5/0077
See application file for complete search history.

(56) References Cited

U.S. PATENT DOCUMENTS

| 8,208,719 B2 | 6/2012 | Gordon et al. |
| 9,943,371 B2 | 4/2018 | Bresch et al. |

(Continued)

FOREIGN PATENT DOCUMENTS

| CN | 111724894 A | 9/2020 |
| JP | 7065361 B2 | 6/2018 |

(Continued)

OTHER PUBLICATIONS

WIPO Appln. No. PCT/KR2022/013642, International Search Report and Written Opinion, Dec. 22, 2022, 12 pg.

(Continued)

*Primary Examiner* — Carolyn A Pehlke
(74) *Attorney, Agent, or Firm* — Kevin T. Cuenot

(57) ABSTRACT

A multimodal, contactless vital sign monitoring system is configured to perform the following operations. Images are received from a video capture device. An image of a subject is identified within the images. The image of the subject is segmented into a plurality of segments. A first analysis is performed on the plurality of segments to identify a color feature. A second analysis is performed of the plurality of segments to identify a motion feature. Using a combination of the color feature and the motion feature a plurality of vital signs for the subject are determined. The first analyzing and the second analyzing are performed in parallel. The plurality of vital signs include one or more of heart rate, respiration rate, oxygen saturation, heart rate variability, and atrial fibrillation.

18 Claims, 18 Drawing Sheets

(56) References Cited

U.S. PATENT DOCUMENTS

| | | | |
|---|---|---|---|
| 10,542,925 B2 | 1/2020 | Kirenko et al. | |
| 10,750,959 B2 | 8/2020 | Gupta et al. | |
| 11,004,223 B2 | 5/2021 | Antoni et al. | |
| 11,276,177 B1 | 3/2022 | Tsai et al. | |
| 11,490,824 B2 | 11/2022 | Watanage | |
| 2009/0306484 A1 | 12/2009 | Kurtz et al. | |
| 2015/0157224 A1* | 6/2015 | Carmon | A61B 5/0205 |
| | | | 600/479 |
| 2015/0302158 A1 | 10/2015 | Morris et al. | |
| 2015/0359443 A1* | 12/2015 | Poh | A61B 5/02405 |
| | | | 600/479 |
| 2016/0066894 A1 | 3/2016 | Barton-Sweeney | |
| 2016/0106327 A1 | 4/2016 | Yoon et al. | |
| 2016/0253820 A1 | 9/2016 | Jeanne et al. | |
| 2017/0238842 A1* | 8/2017 | Jacquel | A61B 5/0205 |
| 2018/0153455 A1* | 6/2018 | Guazzi | A61B 5/02416 |
| 2018/0260952 A1 | 9/2018 | Bagherinia et al. | |
| 2018/0307927 A1 | 10/2018 | Hutchinson | |
| 2019/0041989 A1 | 2/2019 | Wu et al. | |
| 2021/0082109 A1 | 3/2021 | Wu et al. | |
| 2021/0085191 A1 | 3/2021 | Degtyarenko et al. | |
| 2021/0144009 A1 | 5/2021 | Dinkelmann et al. | |
| 2021/0161415 A1 | 6/2021 | Aumer et al. | |
| 2022/0183575 A1* | 6/2022 | Sabbagh | A61B 5/0077 |

FOREIGN PATENT DOCUMENTS

| | | |
|---|---|---|
| KR | 2015-0139700 A | 12/2015 |
| KR | 20160044267 A | 4/2016 |
| KR | 102014093 B1 | 8/2019 |
| KR | 102529120 B1 | 5/2023 |
| KR | 20230084486 A | 6/2023 |
| WO | 14177750 A1 | 11/2014 |

OTHER PUBLICATIONS

EP Appln. No. 22887341.0, Extended European Search Report, Sep. 20, 2024, 7 pg.

Guid et al., "Efficient Real-Time Camera Based Estimation of Heart Rate and its variability," 2019 IEEE/CVF Int'l. Conf. on Computer Vision Workshop (ICCVW), IEEE, Oct. 27, 2019, pp. 1570-1579, xp033732516.

\* cited by examiner

Estimation of HR and vital sign from video: comparing scenario where the whole image is considered for physiological signal process vs. the scenario where multi regions are processed separately and locally

| | Subtask | NormalBreathing-15 | NormalBreathing-10 | CoolDown | Average |
|---|---|---|---|---|---|
| MAE (bpm) | All skin | 4.52 | 9.67 | 7.56 | 7.22 |
| | Multi-Region | 2.25 | 4.98 | 6.03 | 4.28 |

| | MAE RR | |
|---|---|---|
| Ref. RR | All Skin | Multi-Region |
| 5 | 10.37 | 3.50 |
| 10 | 1.57 | 1.77 |
| 15 | 3.53 | 2.17 |
| 20 | 2.00 | 5.22 |
| 25 | 5.87 | 9.22 |
| ALL | 4.617 | 4.38 |

Estimation of RR vital sign from face video: scenario where motion signals are extracted from all points together without localization

| MAE | 5 BPM | 10 BPM | 15 BPM | 20 BPM | TOTAL |
|---|---|---|---|---|---|
| Peaks | 6.40 | 3.69 | 1.97 | 2.34 | 2.88 |
| Zero-crossing | 1.74 | 2.09 | 4.02 | 7.53 | 3.08 |
| FFT (RR) | 2.48 | 2.74 | 1.71 | 4.26 | 2.24 |

FIG. 15A

Estimation of RR vital sign from face video: scenario where motion signals are extracted from each point separately and combined based on SNR values of the motion signal considering the motion artifacts

| MAE | 5 BPM | 10 BPM | 15 BPM | 20 BPM | TOTAL |
|---|---|---|---|---|---|
| Peaks | 6.07 | 3.79 | 1.77 | 2.35 | 2.80 |
| Zero-crossing | 2.17 | 2.06 | 3.86 | 7.36 | 3.09 |
| FFT (RR) | 2.87 | 2.39 | 1.63 | 4.10 | 2.20 |

FIG. 15B

Motion-Based Vital Sign Sensing from Nose, Side Cheeks and Eyebrows Area – some of the regions such as "eyebrows" are more prone to noise due to activities such as emotion expression and blinking

| MAE (MRE, %) | 5 BPM | 10 BPM | 15 BPM | 20 BPM | 25 BPM | TOTAL |
|---|---|---|---|---|---|---|
| Peaks | 6.20 | 3.96 | 1.83 | 2.30 | 4.24 | 3.71 |
| Zero-crossing | 2.23 | 2.17 | 4.02 | 7.64 | 12.17 | 5.65 |
| FFT (RR) | 2.97 | 2.52 | 1.72 | 4.29 | 5.83 | 3.47 |

FIG. 16A

Motion-Based Vital Sign Sensing from Nose and Side Cheeks Area – visual-based target sensing only selects the regions that match the labels which have better vital reading accuracy

| MAE (MRE, %) | 5 BPM | 10 BPM | 15 BPM | 20 BPM | 25 BPM | TOTAL |
|---|---|---|---|---|---|---|
| Peaks | 6.07 | 3.79 | 1.77 | 2.35 | 4.29 | 3.65 |
| Zero-crossing | 2.17 | 2.06 | 3.86 | 7.36 | 11.77 | 5.44 |
| FFT (RR) | 2.87 | 2.39 | 1.63 | 4.10 | 5.45 | 3.28 |

FIG. 16B

Motion-Based Vital Sign Sensing from Nose and Side Cheeks Area plus Chest – visual-based target sensing only selects the regions that match the labels which have better vital reading accuracy

| MAE (MRE, %) | 5 BPM | 10 BPM | 15 BPM | 20 BPM | 25 BPM | TOTAL |
|---|---|---|---|---|---|---|
| Peaks | 3.32 | 1.50 | 1.42 | 1.38 | 2.94 | 2.11 |
| Zero-crossing | 0.89 | 1.11 | 2.15 | 3.98 | 7.19 | 3.06 |
| FFT (RR) | 0.78 | 0.68 | 0.84 | 1.52 | 3.69 | 1.50 |

FIG. 16C

MULTIMODAL CONTACTLESS VITAL SIGN MONITORING

CROSS-REFERENCE TO RELATED APPLICATIONS

This application claims priority to U.S. Provisional Patent Application No. 63/272,084, filed on Oct. 26, 2021, the entirety of which is incorporated herein by reference.

TECHNICAL FIELD

This disclosure relates to monitoring of vital signs, and more particularly, to a system and methodology of monitoring multiple vital signs using video using multiple modes.

BACKGROUND

Continuous measurement of vital signs such as heart rate (HR), respiration rate (RR), heart rate variability (HRV), and oxygen saturation (SpO2) is often used to monitor an individual's cardiovascular, respiration, and physical health. Continuous monitoring of these vital signs can provide useful insight for clinicians to diagnose and track progress of a condition as the vital signs provide a snapshot of the inner workings of a subject's body. Additionally, these metrics can be beneficial in analyzing an individual's current fitness and progress over time.

Conventional approaches for obtaining vital signs involve medical devices with contact sensors used to monitor these vital signs. For example, respiration belts can use motion or force sensors to monitor the motion of chest movement and measure the respiration rate. Additionally, LED sensors with IR light have been used to monitor the blood volume flow through fingertips of users as well as continuously measuring heart rate and oxygen saturation levels.

There are, however, multiple problems with the current devices used to monitor vital signs. For example, when dedicated hardware and specific sensors are used to measure each vital sign, the total cost of a device can increase. Additionally, these devices require continuous contact with the subject (e.g., on the face, skin, fingertip, wrist, and/or chest), which can cause skin irritation/damage, impede mobility of the user, be a vector for cross-contamination of viruses between users, be erroneous due to uncontrolled motions of the device, and generally by uncomfortable to a user when sensors/wires are placed on the user.

Current contactless vital sign monitoring systems that analyze color features of a face image to extract physiological signals (e.g., vital signs) address some of the issues regarding device that require continuous contact with the subject. However, these contactless systems have reduced performance in situations in which the face image is not segmented properly, lighting conditions impact the face image, different levels of shows are presented on the face, and/or a user is involved in physical activity. Consequently, there is a need for an improved contactless vital signing monitoring system that does not require individualized hardware sensors and can adjust to varying environmental/lighting conditions to provide accurate results.

SUMMARY

In an example implementation, a multimodal, contactless vital sign monitoring system is configured to perform the following operations. Images are received from a video capture device. An image of a subject is identified within the images. The image of the subject is segmented into a plurality of segments. A first analysis is performed on the plurality of segments to identify a color feature. A second analysis is performed of the plurality of segments to identify a motion feature. Using a combination of the color feature and the motion feature a plurality of vital signs for the subject are determined. The first analyzing and the second analyzing are performed in parallel.

Other aspects of this example implementation include the first analyzing: establishing, for each of the plurality of segments, a baseline value for each of the plurality of segments, determining, for each of the plurality of segments, a segment value by comparing a detected value to the baseline value, and identifying the color feature based upon a combination of the segment values. The plurality of segments can be classified into a first classification and a second classification, and the plurality of segments are filtered based upon the first classification and the second classification. Also, the establishing of the baseline value and the segment value are performed only for the plurality of segments classified into the first classification.

The second analyzing can include identifying a plurality of landmarks of the subject visible in the image of the subject, identifying, for each of the plurality of landmarks, a movement over a plurality of images of the subject, and identifying the motion feature based upon a combination of the movements of the landmarks. The second analyzing can also include identifying a motion artifact not associated with the plurality of vital signs, and excluding, from the identifying the motion feature, the motion artifact.

In other aspects, a plurality of subjects are found within the images, and a particular one of the plurality of subjects is selected to be the subject. Also, the color feature and the motion feature are weighed based upon signal quality and motion intensity. The video capture device can be integrated into the contactless vital sign monitoring system and/or external to the contactless vital sign monitoring system. The plurality of vital signs include one or more of heart rate, respiration rate, oxygen saturation, heart rate variability, and atrial fibrillation.

In another example implementation, a method is performed. Images are received from a video capture device. An image of a subject is identified within the images. The image of the subject is segmented into a plurality of segments. A first analysis is performed on the plurality of segments to identify a color feature. A second analysis is performed of the plurality of segments to identify a motion feature. Using a combination of the color feature and the motion feature a plurality of vital signs for the subject are determined. The first analyzing and the second analyzing are performed in parallel.

This Summary section is provided merely to introduce certain concepts and not to identify any key or essential features of the claimed individual matter. Other features of the inventive arrangements will be apparent from the accompanying drawings and from the following detailed description.

BRIEF DESCRIPTION OF THE DRAWINGS

The inventive arrangements are illustrated by way of example in the accompanying drawings. The drawings, however, should not be construed to be limiting of the inventive arrangements to only the particular implementations shown. Various aspects and advantages will become apparent upon review of the following detailed description and upon reference to the drawings.

FIGS. 15A-B are, respectively, a table in which motion signals are extracted from all points together without localization and where motion signals are extracted from each point separately and combined based on SNR values of the motion signal considering motion artifacts, according to an embodiment.

FIGS. 16A-C are tables illustrated mean average error based upon three different scenarios, according to an embodiment.

DETAILED DESCRIPTION

Figure 1:
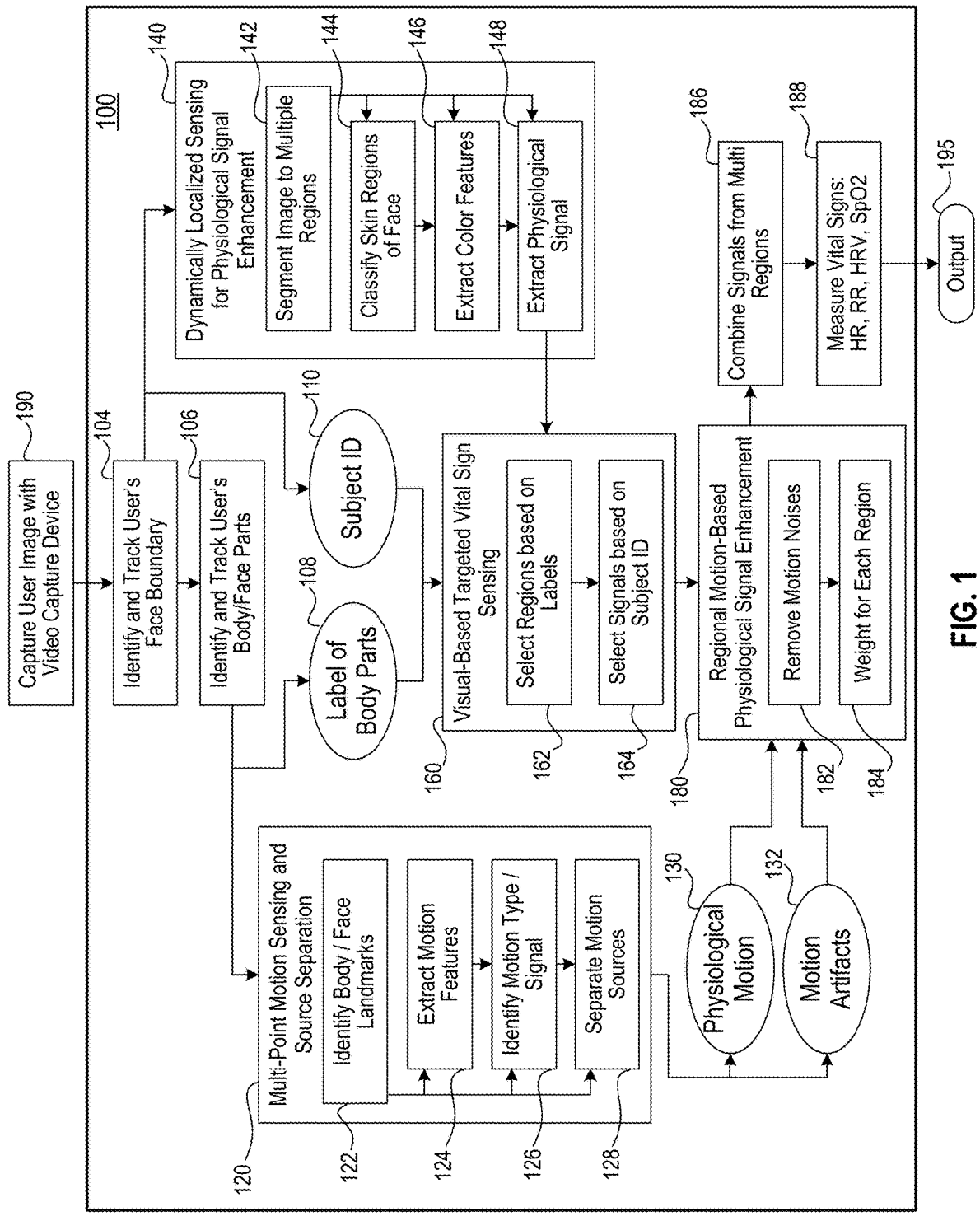
FIG. 1 is a block diagram illustrating different aspects of a multimodal, contactless vital sign monitoring system, according to an embodiment.

FIG. 1 illustrate different aspects of a multimodal, contactless vital sign (MCVS) monitoring system 100 according to the disclosure. In general, the MCVS monitoring system 100 is configured to determine, continuously or periodically, vital signs of an individual, such as heart rate (HR), respiration rate (RR), heart rate variability (HRV), oxygen saturation (SpO2), blood pressure, and atrial fibrillation (AFib) from physiological signals extracted from an image sequence (e.g., a video) recorded by a video capture device 190. Although not limited in this precise manner, the MCVS monitoring system 100 can include four specialized subcomponents 120, 140, 160, 180, and aspects of these subcomponents 120, 140, 160, and 180 are discussed below.

Using the video capture device 190, visual features correlated with a subject's cardio-respiratory system can be captured. For example, temporal variations of the subject's skin color caused by the changes in blood pulse volume can be monitored (color modality). Additionally, the MCVS monitoring system 100 can be configured to identify visual motion in the user's body as well as to monitor facial landmarks to obtain motion data also reflective of the subject's cardio-respiratory system (motion modality). The MCVS monitoring system 100 combines data from both motion and color modalities to achieve a higher quality physiological signal thereby generating more accurate vital signs of the subject.

Although not limited in this manner, the video capture device 190 can use RGB sensors. In a RGB-capable device, each sensor is configured to capture different primary colors (i.e., Red, Green, and Blue) and the data captured by each sensor is added together to arrive at a resultant image. Examples of devices that can include a video capture device 190 are a smart TV, tablet, laptop, and smartphone. The MCVS monitoring system 100 can natively include the video capture device 190 and/or the MCVS monitoring system 100 can receive image data from an external video capture device 190.

Modules 104-110 can provide conventional functionality for the MCVS monitoring system 100, and the MCVS monitoring system 100 is not limited in the manner by which this functionality is provided. Although illustrated as being separate, the described functions of these modules 104-110 can be consolidated into one or more modules. After an image has been received from the video capture device 190, those portions of the image that display a subject (i.e., a user/individual) are identified. From these portions, in module 104, a boundary defining the subject's face can be identified and tracked. Similarly, in 106, individual portions of the subject's body and face can be identified and tracked. These individual portions can then be labeled in module 108. Additionally, in module 110, a specific identity of the subject (subject ID) can be identified using the subject's face. For example, a machine learning model can be employed to distinguish users' identities based on their facial/body structure. Certain portions of this information can then be passed onto the subcomponents 120, 140, 160.

Dynamically Localized Sensing for Physiological Signal Enhancement

General aspects of the dynamically localized sensing for physiological signal enhancement separation (hereinafter referred to as the dynamic segmentation and enhancement engine 140) are illustrated in FIG. 1. The dynamic segmentation and enhancement engine 140 can include a machine learning engine 142 that is configured to segment multiple regions of interest (ROIs), which are also referred to herein as segments. The dynamic segmentation and enhancement engine 140 can also include a portion 144 configured to identify skin regions of the received image. The dynamic segmentation and enhancement engine 140 can also include a portion 146 configured to extract color features from the skin regions identified by portion 144. As used herein, the term "color features" refers to color-based image data extracted from an image. The dynamic segmentation and enhancement engine 140 can also include a portion 148 configured to extract physiological signals (i.e., vital signs) from the color features extracted by portion 146. The extracted physiological signals for each ROI/segment can then be forwarded to the targeting engine 160.

Figure 2:
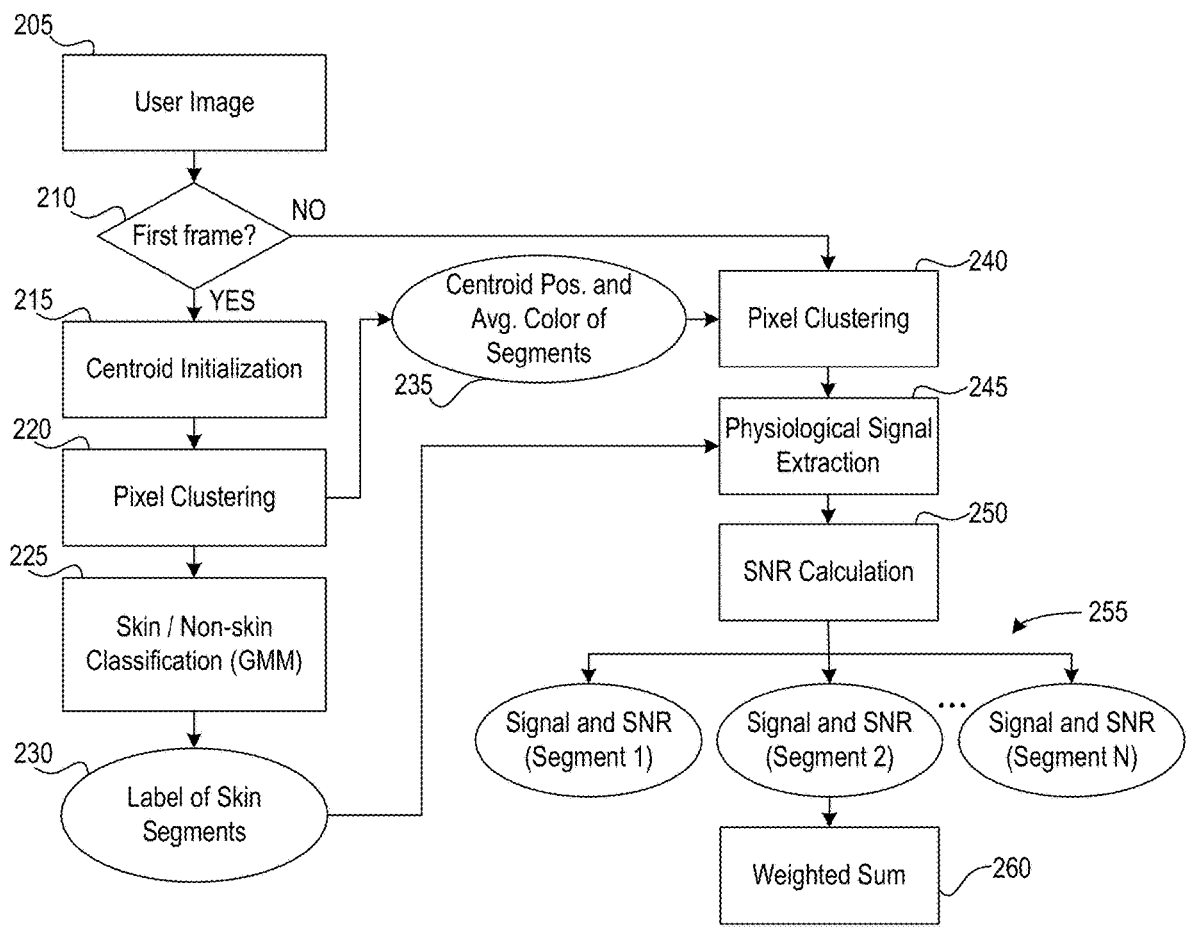
FIG. 2 is a flowchart of an example method using the dynamic segmentation and enhancement engine illustrated in FIG. 1, according to an embodiment.
Figure 3B:
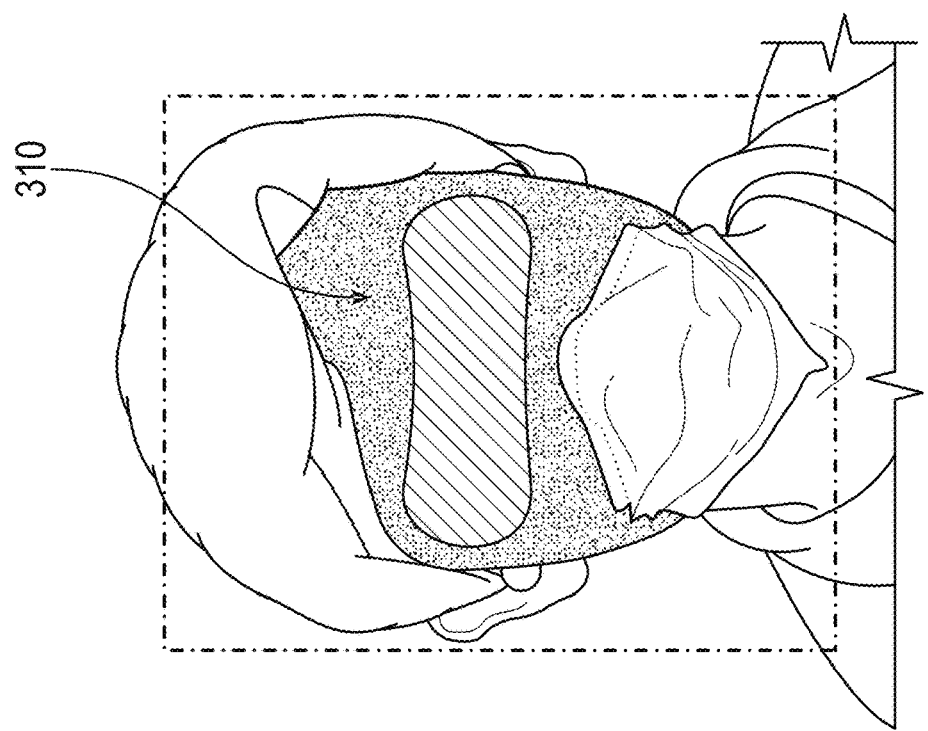
FIGS. 3A-B illustrate, respectively, an image of a face being segmented into regions of interest and an image of a face in which certain regions of interest are classified as skin segments, according to an embodiment.
Figure 3A:
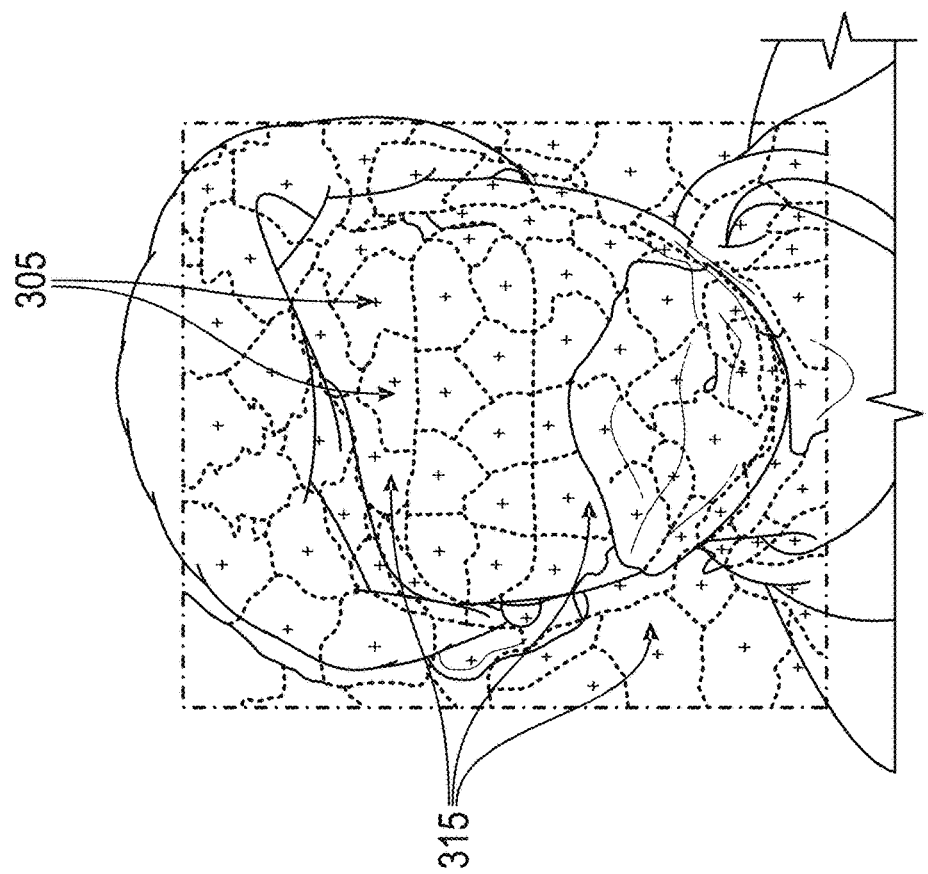

FIGS. 2 and 3A-B further elaborate on the dynamic segmentation and enhancement engine 140. Specifically, FIG. 2 is a flowchart of an example method using the dynamic segmentation and enhancement engine 140. In block 205, the video image of a user is captured using the image capture device 190. After a determination is made in block 210 that a frame of the video image being analyzed is the first frame, a number of specialized operations 215-235 are performed. The image can be segmented into multiple regions of interest (ROIs) based upon both color and space proximity using conventional techniques. An example of an image of a face being segmented into ROIs/segments 315 is illustrated in FIG. 3A.

In block 215, a centroid position and average color of each segment 315 can be calculated, and the manner in which the centroid position 305 and average color is determined is not limited as to a particular technique. In block 220, the pixels associated with each segment 315 are clustered together based on color and space proximity. In block 235, the centroid position 305 and the average color for each segment/cluster 315 and can be tracked over time with this information being used during the analysis of subsequent frames.

In block 225, the machine learning engine 142 can classify the segments 315, for example, as either skin 310 or not skin. The machine learning engine 142 is not limited in manner by which the segments 315 are classified. For example, the skin classification can be performed using Gaussian Mixture Model (GMM) or Convolutional Neural Networks (CNN). Once each segment 315 has been classified, a label of either skin or not skin is applied to each of the segments 310 in block 230. As illustrated in FIG. 3B, all of the skin segments 310 can be identified.

In subsequent frames, operations 240-260 are performed, and in certain aspects, these operations are only performed for the skin segments 310. In block 240, the pixels from each of the segments 315 are clustered together, and in block 245, the physiological signal is extracted for each of the segments 315. Although not limited in this manner, the physiological signals (i.e., vital signs) are captured for each of the segments 315 by monitoring temporal variations of the skin color caused by the changes in blood pulse volume using, for example, photoplethysmography (PPG). Additionally, as is conventionally known, PPG can also be used to monitor respiration rate (RR). In block 250, a signal to noise ratio (SNR) for each physiological signal is extracted.

In block 255, the segments/ROIs 305 are dynamically segmented based on the color and spatial features, and the physiological signals corresponding to each segment/ROI 315 can be evaluated with respect to its own baseline value and variation of pixel colors. Physiological signals from different segments/ROIs 315 of the body and face can be extracted in parallel and processed together to compensate for the differences in the signal baseline values and variation due to differences in variables such as blood perfusion level, lighting conditions, and presence of shadow. In block 260, the processed physiological signals from each of the segments and their respective SNR values can be weighted and combined to enhance the quality final conglomerated physiological signal, and thus, the accuracy of the measured vital signs.

Multi-Point Motion Sensing and Source Separation

General aspects of the multi-point motion sensing and source separation (hereinafter referred as the motion sensing engine 120) are illustrated in FIG. 1. The motion sensing engine 120 can include a portion 122 configured to identify, in parallel, multiple landmarks/points on the body and/or face of the user and these landmarks/points are tracked over time using techniques such as optical flow tracking. The motion sensing engine 120 can also include a portion 124 configured to analyze the tracked points/landmarks to extract motion features corresponding to each tracked point/landmark. As used herein, the term "motion features" refers to motion-based image data extracted from an image. The motion sensing engine 120 can also include a portion 126 configured to process the motion features to identify a type of motion corresponding to the particular point/landmark being analyzed. The motion sensing engine 120 can also include a portion 128 configured to identify separate sources contributing to the motion feature. In so doing, the motion sensing engine 120 can distinguish between motion artifacts 132 (e.g., talking, head movements, laughing, coughing) and physiological activity data 130 (e.g., data representative of breathing or heart beating) that can be used to determine vital signs.

The motion sensing engine 120 is configured to output physiological activity data 130 used for determining vital signs as well as data 132 for identifying motion artifacts in particular regions of the body. In separating the motion artifact data 132 from the physiological activity data 130, a higher-quality determination of vital signs can be performed using the physiological activity data 130.

Figure 4B:
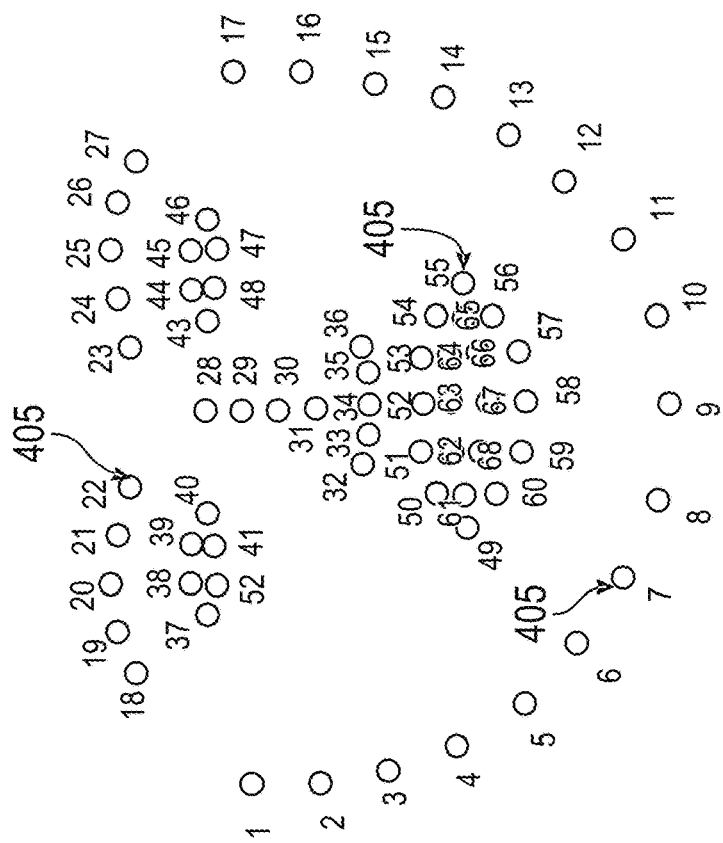
FIGS. 4A-B illustrate, respectively, an image of a face in which facial landmarks are identified and a collection of the identified facial landmarks, according to an embodiment.
Figure 4A:
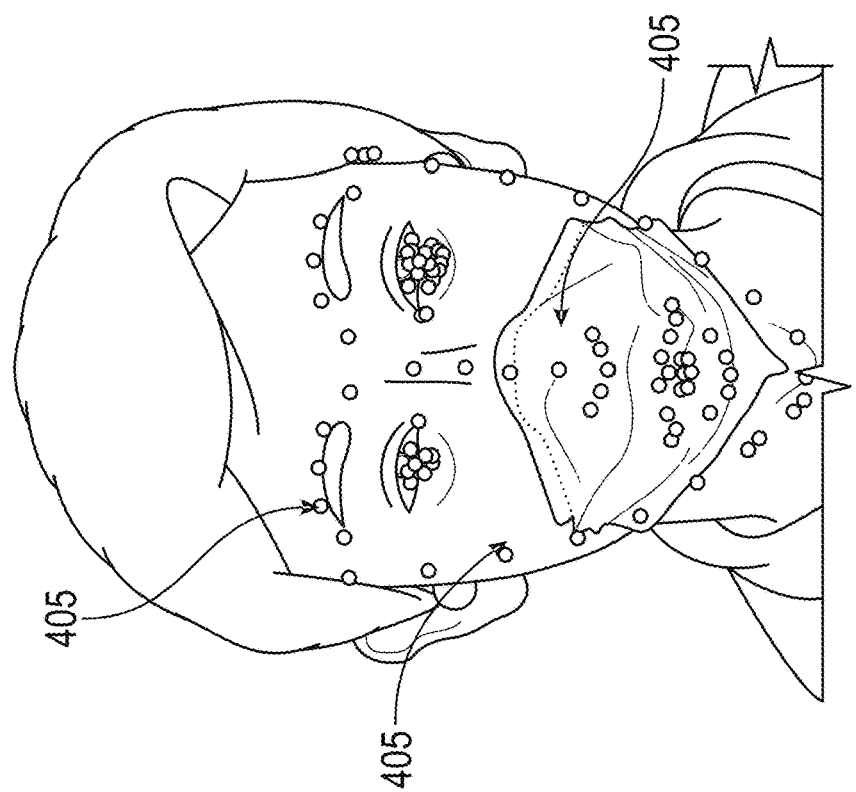

FIGS. 4A-B, 5A-B, 6A-B illustrate aspects of the motion sensing engine 120. Referring to FIG. 4A, using a received image, multiple points/landmarks 405 on the body/face are identified and tracked for extracting motion features related to motion artifacts or physiological activities. Conventional techniques for identifying points/landmarks 405 on the body/face may be applied, and the motion sensing engine 120 is not limited to a particular technique. FIG. 4B illustrates the points/landmarks 405 that were identified from FIG. 4A.

Figure 5B:
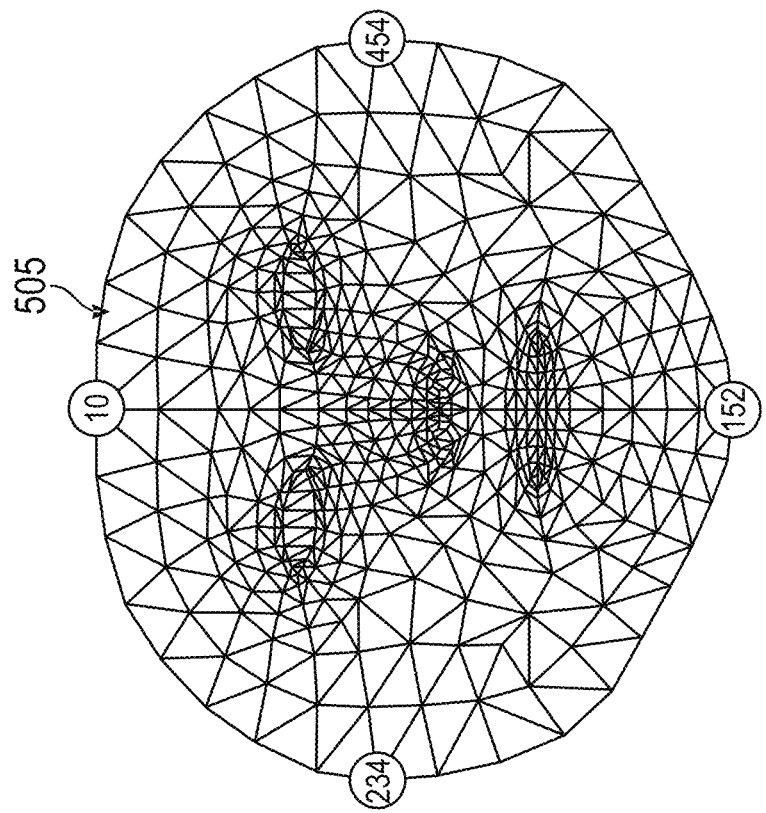
FIGS. 5A-B illustrate, respectively, an image of a face in which a 3D mesh of landmarks are identified and the 3D mesh, according to an embodiment.
Figure 5A:
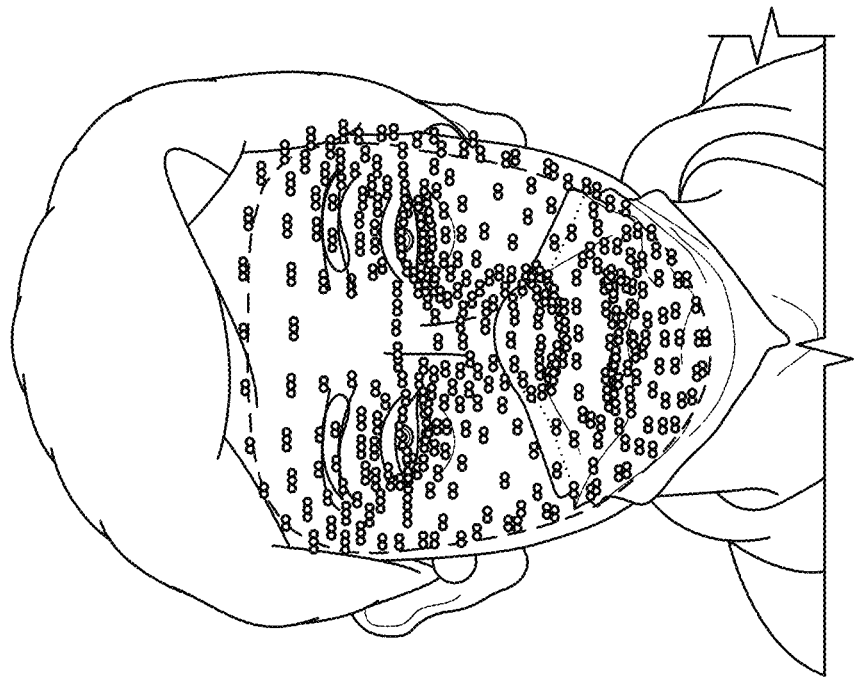

Movement of head and/or different points on the face can provide information of physiological motions (e.g., breathing or heart beating) and other activities of the user such as laughing, coughing, or talking. In certain aspects, the structure or color features in the image are processed to find a match with a human face to identify and track the individual's face. Known facial landmark detection techniques can be used to further analyze the image and extract placement of multiple landmarks on the face such as eyes, nose, cheeks, and mouth. In other aspects, a machine learning model can be used to detect face and the landmarks 405 at the same time. As illustrated in FIGS. 5A-B, more complex models can provide a 3D mesh 505 comprising a plurality of points representing the face structure and position of the landmarks.

Figure 6B:
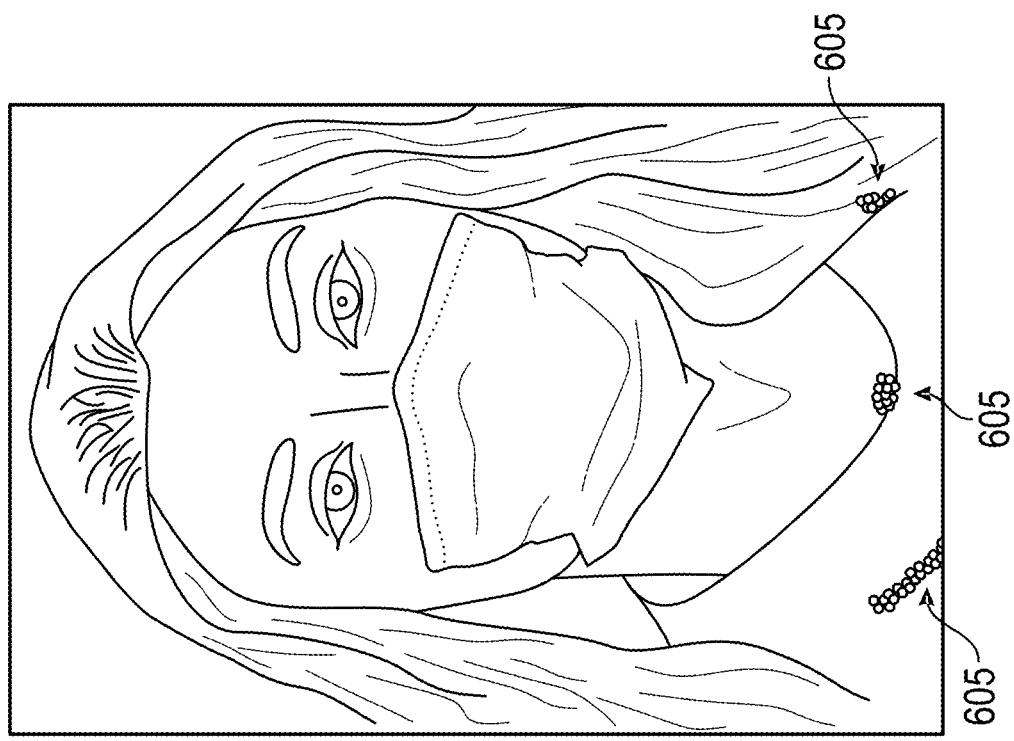
FIGS. 6A-B illustrate, respectively, images of two faces in which three points on the upper chest of the subjects are identified and tracked, according to an embodiment.
Figure 6A:
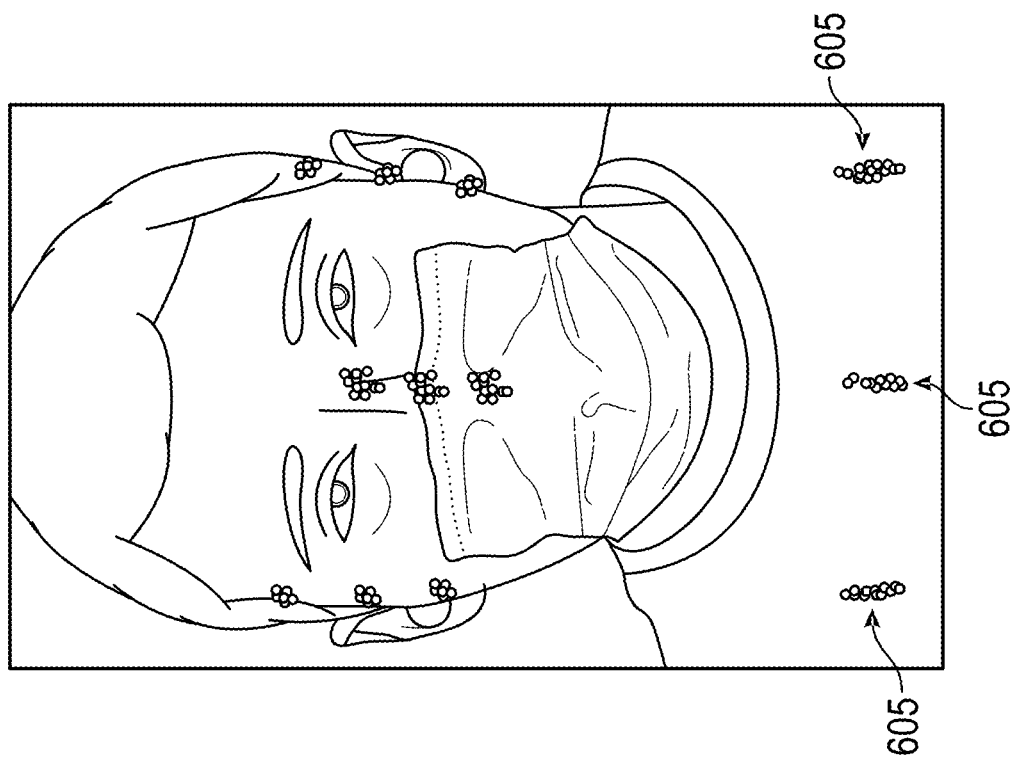

Referring to FIGS. 6A-B, besides the face, movement of body parts such as upper chest and shoulder area can also be correlated with physiological activities such as breathing or heart beating. In certain aspects, a position of these body parts can be identified with respect to a position of the face during facial identification and tracking. In another aspect, using machine learning models, the body parts can be identified directly by analyzing the image to find a structure similar to the upper chest or shoulder. As illustrated in FIGS. 6A-B and by way of example, three points 605 on the upper chest and shoulder area are identified and tracked. The estimated movement of each point 605 for a short period of time is illustrated with a line associated with each point 605.

The identified points/landmarks 505, 605 can be tracked separately throughout a video recording to extract and estimate motion signals. In certain aspects, the points 505, 605 can be tracked using an optical flow tracking technique whereby consecutive images are compared together to evaluate how far an individual points/landmark has moved. The color and brightness of image surrounding the points/landmarks 505, 605 can be analyzed to find regions with similar characteristics in the consecutive frames, and the minimum distance of movement can then be estimated by displacing the frames.

Figure 7:
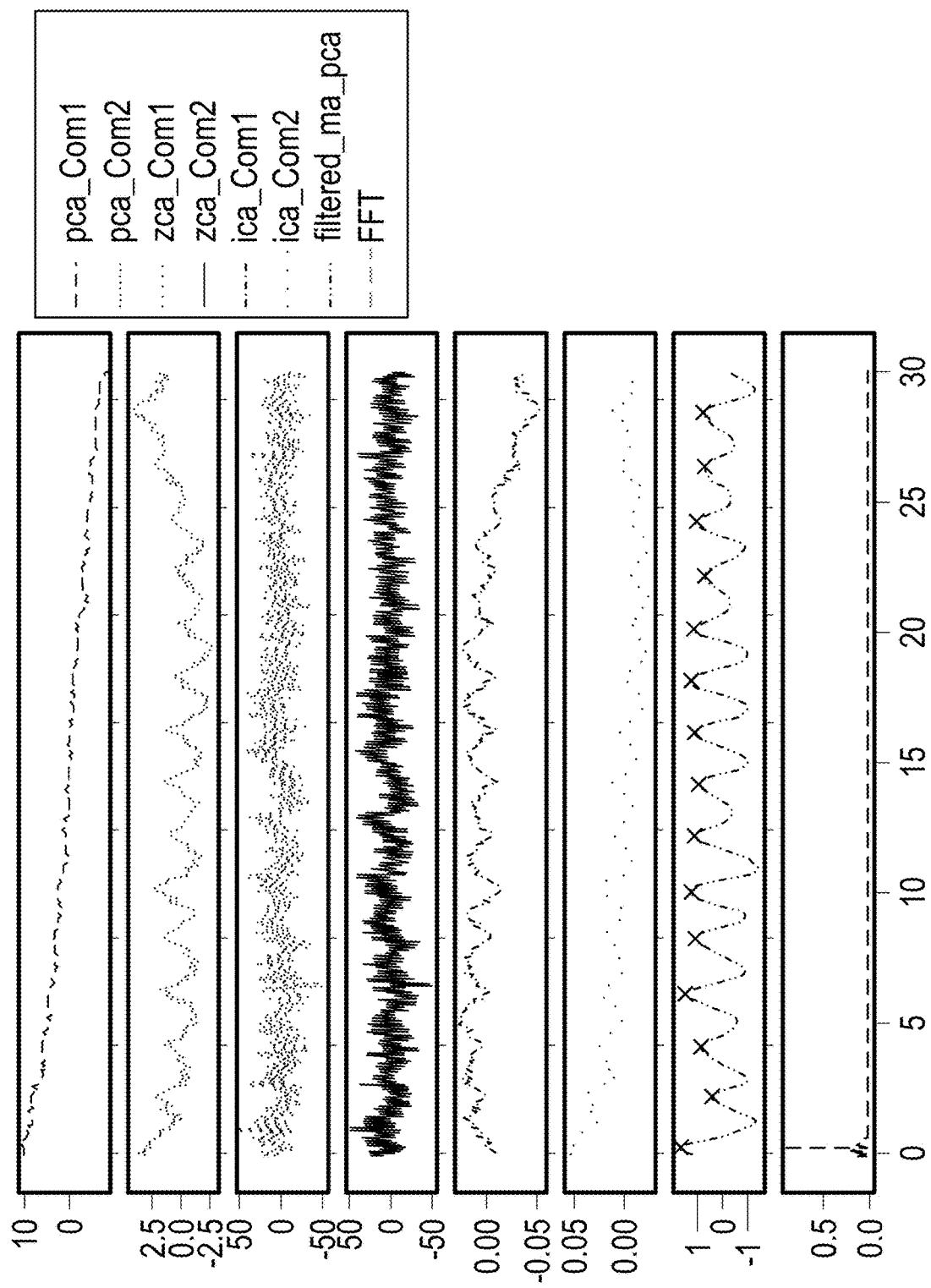
FIG. 7 is a graph illustrating motion signal enhancement and preprocessing operations.
Figure 8:
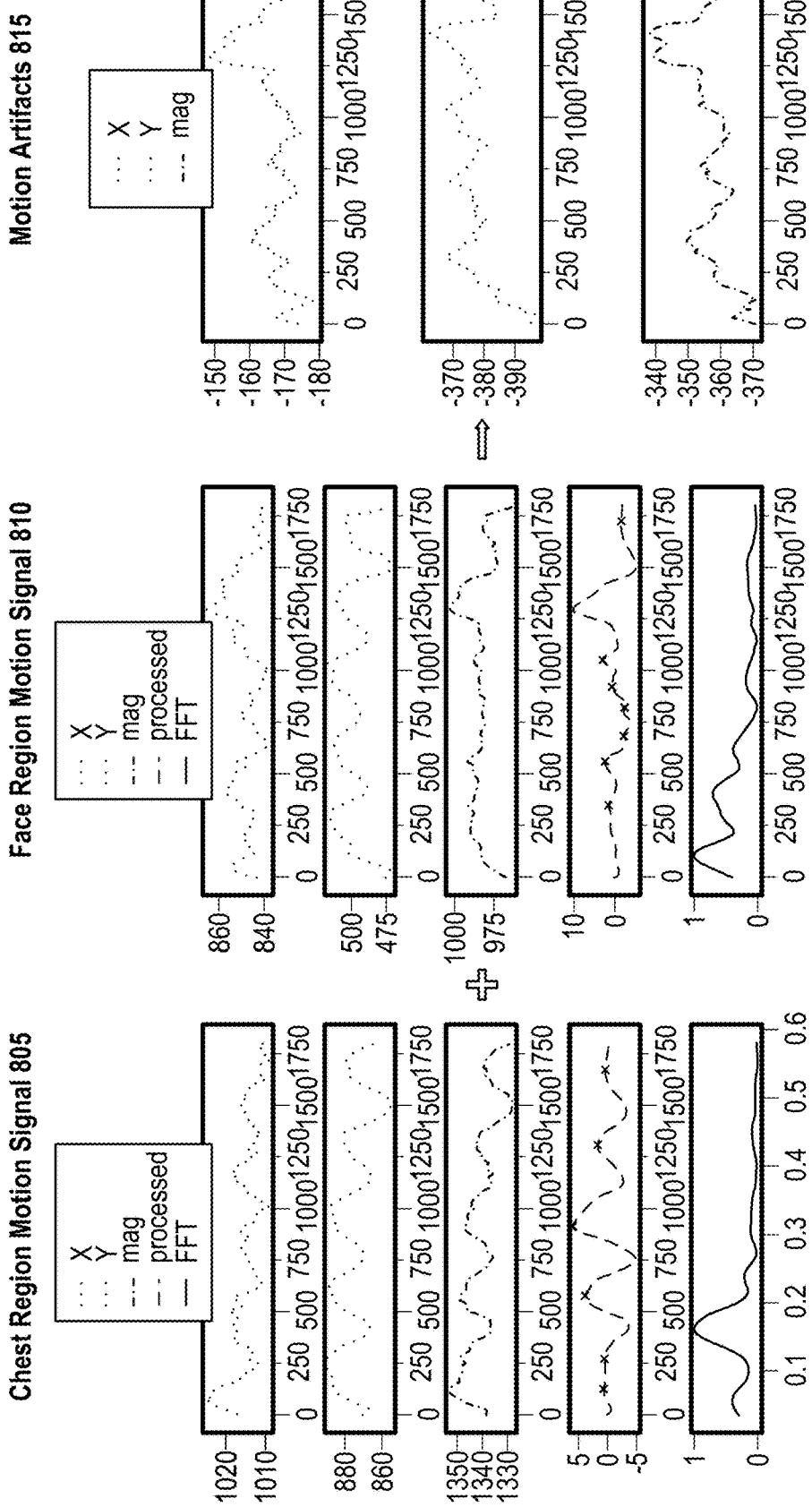
FIG. 8 illustrates graphs illustrating motion signals from face regions and upper chest regions being processed to find a common physiological component, according to an embodiment.

FIGS. 7 and 8 illustrate further aspects of the motion sensing engine 120, which fuses together regional motion signals from multiple points of the body to generate an enhanced motion signal and separate physiological signals from different sources. As illustrated in FIG. 7, regional motion signals are separately processed with respect to their own baseline and variation of the movement in 2D space. The separation of the motion signals improves the measurement of vital signs by being more resilient towards motion noise. Each motion signal can be estimated in X and Y dimensions and combined to evaluate the magnitude of movement in space. The motion signals are then pre-processed to remove DC components, noise, and frequency components outside of a typical physiological range. The pre-processing steps can include any number of techniques such as detrending, moving average, hamming window, and low/mid/high pass filters.

The processed motion signals can contain physiological motion signals and noises due to motion artifacts. In certain aspects, physiological signals from all regions/segments are combined and processed to find the principal component and common signal across all regions correlated with physiological motion; the extracted signal can be processed to measure vital signs. In a scenario where the motion is negligible, the average of physiological motion signals can be directly processed to extract the corresponding vital signs.

With reference to FIG. 8, in the presence of motion artifacts, the motion sensing engine 120 can be configured to identify the motion types and separate the motion sources. In certain aspects, using (independent component analysis) ICA/(principal component analysis) PCA techniques or machine learning models, the motion signals from face regions 810 and upper chest regions 805 are processed to find a common physiological component 815 in both regions and remove the component correlated with noise. The pattern of the motion artifact can be analyzed in temporal or frequency domain to identify the physical activity of the observed motion. The extracted motion signal due to motion artifacts can be later used to enhance the color-based physiological signal.

Visual Based Target Vital Sign Sensing

General aspects of the visual-based target vital sign sensing (hereinafter referred to as the targeting engine 160) are illustrated in FIG. 1. The targeting engine 160 is configured to receive the color-based physiological signals extracted by the dynamic segmentation and enhancement engine 140. The targeting engine 160 can include a portion 162 configured to select specific segments/ROIs. The targeting engine 160 can also include a portion 164 configured to select one or more individuals from a plurality of possible individuals based upon subject ID provided by module 110.

The targeting engine 160 can be configured to determine vital signs only from specific regions of the user and/or from specific user(s). For example, in a crowded room the targeting engine 160 may select, from multiple individuals, only a single individual from which to determine vital signs. The visual features, shape, and facial structure of the user's face or segmented images and labels of each body parts can be leveraged to select and filter the physiological signals to be used in determining the final vital signs. This selection can be performed, for example, based upon a prior requirement involving privacy concerns and/or to achieve a more reliable reading of the vital signs. Although not limited in this manner, certain visual features such as intensity of shadow, brightness, perspiration, oiliness, make up, or coverage can be the basis by which a particular segment/ROI is selected from a plurality of segments/ROIs.

Referring to 162, different regions and parts on face/body can be identified based on their color, shape, and structure, for example, using a machine learning model. This additional context can be used to provide a label for the physiological signal being extracted from each segment/ROI. Using a preexisting list and/or based on measurement reliability, each segment/ROI can be either selected or removed from the processing used to determine the final physiological signal. By way of example, vital signs can be more accurately sensed by focusing on more motionless parts of the body. Furthermore, color features such as shadow or brightness, skin characteristics such as perspiration level, oiliness, and ratio of coverage can be used as a set of features to decide which ROIs/segments should be selected or not.

Referring to 164, a scenario exists in which multiple users could be present within the images provide by the video capture device 190. Using the previously provided subject IDs from 110, the targeting engine 160 can filter physiological signals extracted from the image and focus on a specific person(s). In so doing, the MCVS monitoring system 100 can be configured to provide personalized and/or multi-user vital sign sensing using only a single video capture device 190.

Regional Motion-Based Physiological Signal Enhancement

General aspects of the regional motion-based physiological signal enhancement (hereinafter referred to as the motion-based enhancement engine 180) are illustrated in FIG. 1. As previously discussed, the motion-based enhancement engine 180 receives physiological activity data 130 used for determining vital signs and motion artifacts 132 from the motion sensing engine 120. The motion-based enhancement engine 180 can include a portion 182 configured to exclude data 132 associated with the motion artifacts from further analysis as being noise. The motion-based enhancement engine 180 can include a portion 184 that combines the physiological activity data 130 with the color-based physiological data received from the targeting engine 160.

The labels applied by the targeting engine 160 can be used by the motion-based enhancement engine 180 as part of a weighting function. Although not limited in this manner, the weighting function can reflect a determined quality of the physiological signal with respect to motion presence. The MCVS monitoring system 100 can also include a module 186 in which a weighting function used to combine the physiological signals from multiple regions is created. The MCVS monitoring system 100 can include a module 188 that determines the vital signs based upon the weighting function created in module 186. These vital signs can then be outputted via module 195. The output could be, for example, to a local graphical user interface (not shown) associated with the MCVS monitoring system 100 and/or a remote server system (not shown).

The motion-based enhancement engine 180 is configured to leverage the type and pattern of motion identified for each dynamically selected regions of the body/face for adjusting the process of physiological signal extraction based on color for each of the regions. Additionally, the motion-based enhancement engine 180 can compensate the color-based physiological signal for a particular region using a motion pattern associated with the same particular region by, for example, aligning the image sequence considering the motion signal or adjusting the signal processing steps (i.e., filtering) to eliminate motion artifacts. Additionally, the type and pattern of motion identified for each dynamically selected regions of the body/face can be leveraged to adjust the process of combining the physiological signals from the multiple regions using module 186.

In certain aspects, the type and pattern of motion can be used as a flag to start/stop vital sign measurement. This can occur, for example, when a user is detected to be present in a room and continuous video recording is not possible due to privacy concerns. As another example, a flag to start vital measurement can be set when the subject is motionless (i.e., still) enough to provide an accurate reading of vital signs.

Figure 9A:
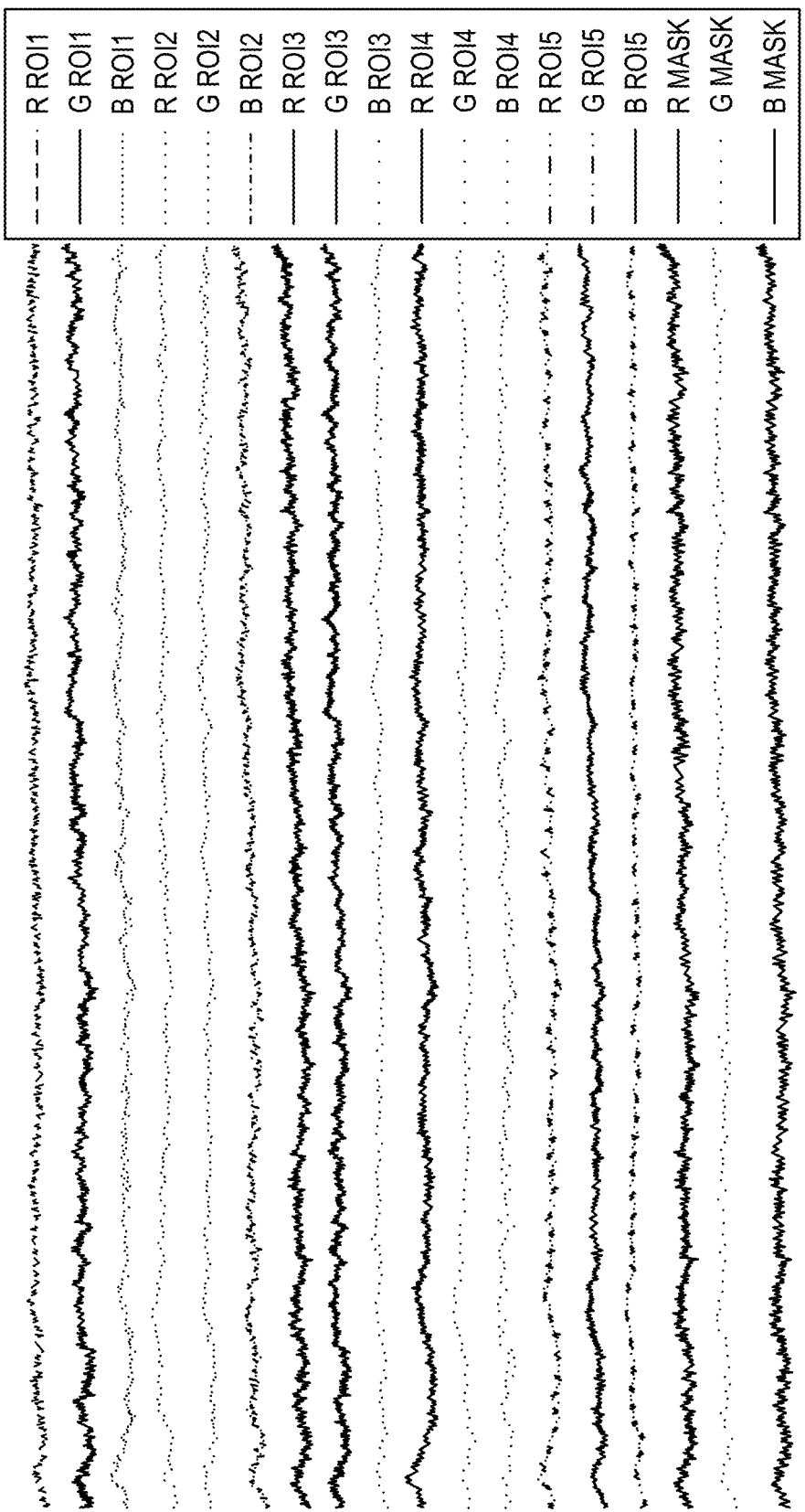
FIGS. 9A-B illustrate, respectively, a graph illustrating physiological signals extracted from red, green, and blue color features of each region on the face and a chart highlighting the weight of each principal component for each of the signals, according to an embodiment.
Figure 9B:
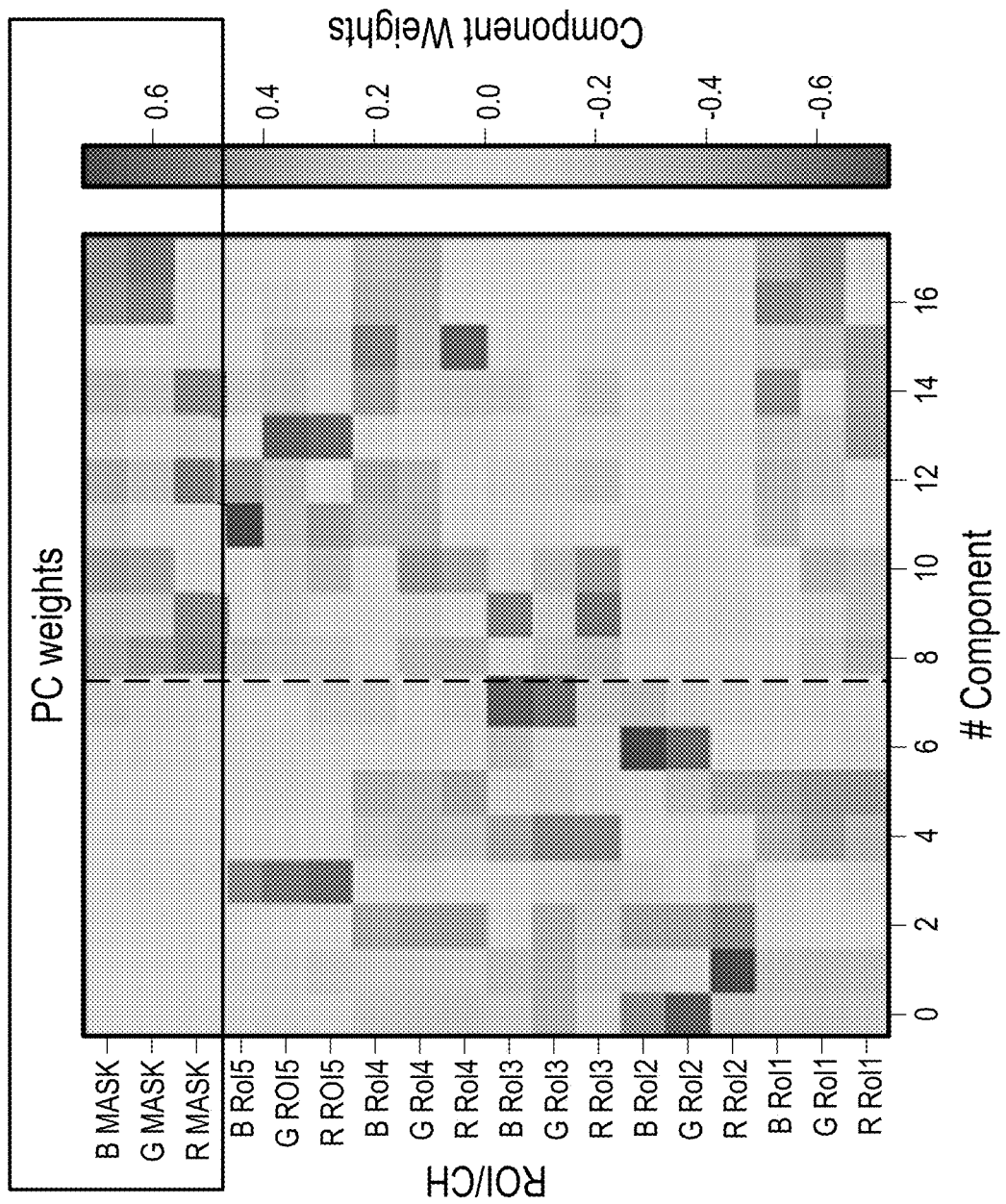

FIGS. 9A-B illustrate aspects of the motion-based enhancement engine 180. PCA/ICA signal decomposition can be used to improve the physiological signals using the physiological activity data 132 and the motion artifacts 132 for the ROIs/segments. Consistent with discussions above, the light reflected (and captured by the dynamic segmentation and enhancement engine 140) is comprised of an array of orthogonal/independent components, which can include blood volume oscillation, motion-based variation related to physiological signals (e.g., breathing, heartbeat, etc.), motion artifacts (i.e., body movement that are not related to the physiological phenomenon), and variation of the lighting condition. Variation in blood volume oscillation, which is used to extract vital signs, is uniformly modulated (with different weights) only in the color changes on the skin ROIs. Subtle motion-based variation related to physiological signals, and the motion artifacts, are modulated in the color changes on both the skin and non-skin ROIs, with different weights. The motion-based enhancement engine 180 is configured to extract the physiological signals from multiple segments/ROIs and include both skin related and non-skin related regions.

The ICA can be applied to decompose multi-region physiological signals into different independent components that include: components related to blood volume oscillation (having significantly lower weights on the non-skin region), components related to subtle motion-based physiological phenomenon (having larger weights on the skin related regions and lower weights on the non-skin region), and components related to motion artifacts (i.e., unrelated body movement), which have significantly lower weights on both skin and non-skin regions. A machine learning model can be trained to classify the components of the physiological signals into the three groups. The motion artifacts can then be eliminated, and the remaining components can be then re-projected to the original color space for vital sign extraction.

Figure 10B:
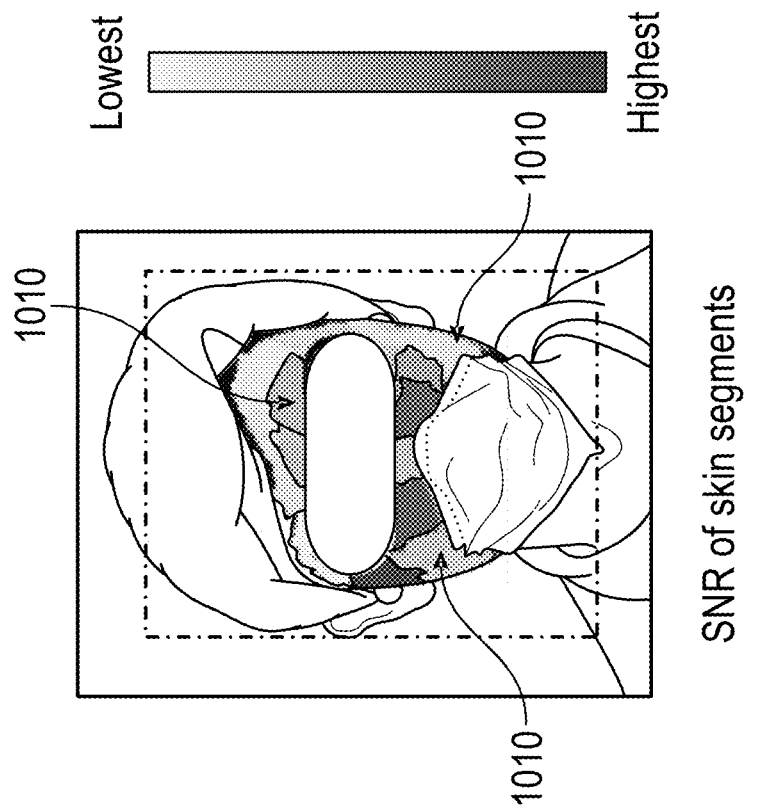
FIGS. 10A-B illustrate, respectively, a graph illustrating a signal-to-noise ratio (SNR) and an image illustrating how the SNR ratio varies based upon a particular skin segment, according to an embodiment.
Figure 10A:
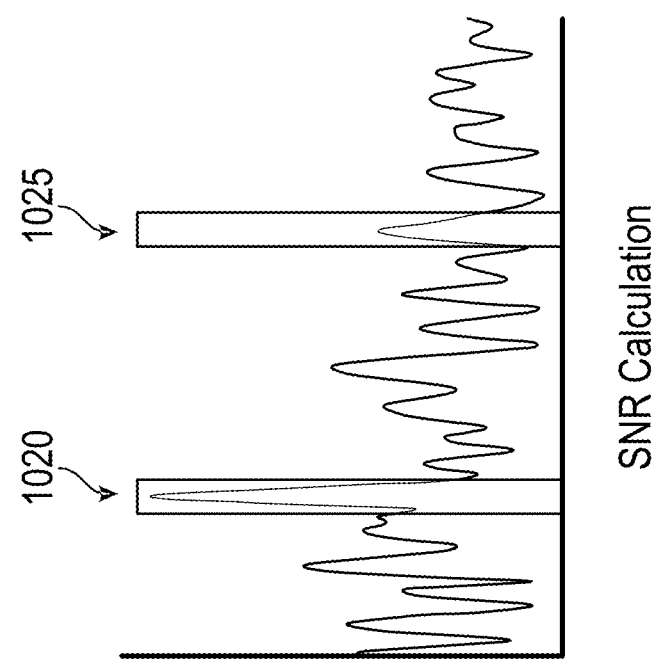

FIGS. 10A-B illustrate further aspects of the motion-based enhancement engine 180. To combine the physiological signal extracted from each of the multiple regions 1010, the signal-to-noise ratio (SNR) of the signal from its spectrum, i.e., the ratio of the energy around the frequency of the highest peak 1020 plus its first harmonics 1025 and the remaining energy in the spectrum is calculated for each segment 1010. The motion-based enhancement engine 180 determines the amount of motion observed in a particular region/segment based upon the SNR of the physiological signal determined for a particular segment.

As illustrated in FIG. 10B, the SNR of the physiological signal for each segment 1010 can vary, and based upon this variance the value for each segment 1010 can be weighted. For example, segments 1010 with higher SNR values can be ranked higher and segments 1010 with lower SNR values can be ranked lower. Accordingly, when the signals are combined using module 186 to determine a single physiological signal value, those segments with higher SNR values will be more impactful. Although not limited to this particular approach, in certain aspects, the weight for a particular segment 1010 is the normalized SNR.

Figure 11:
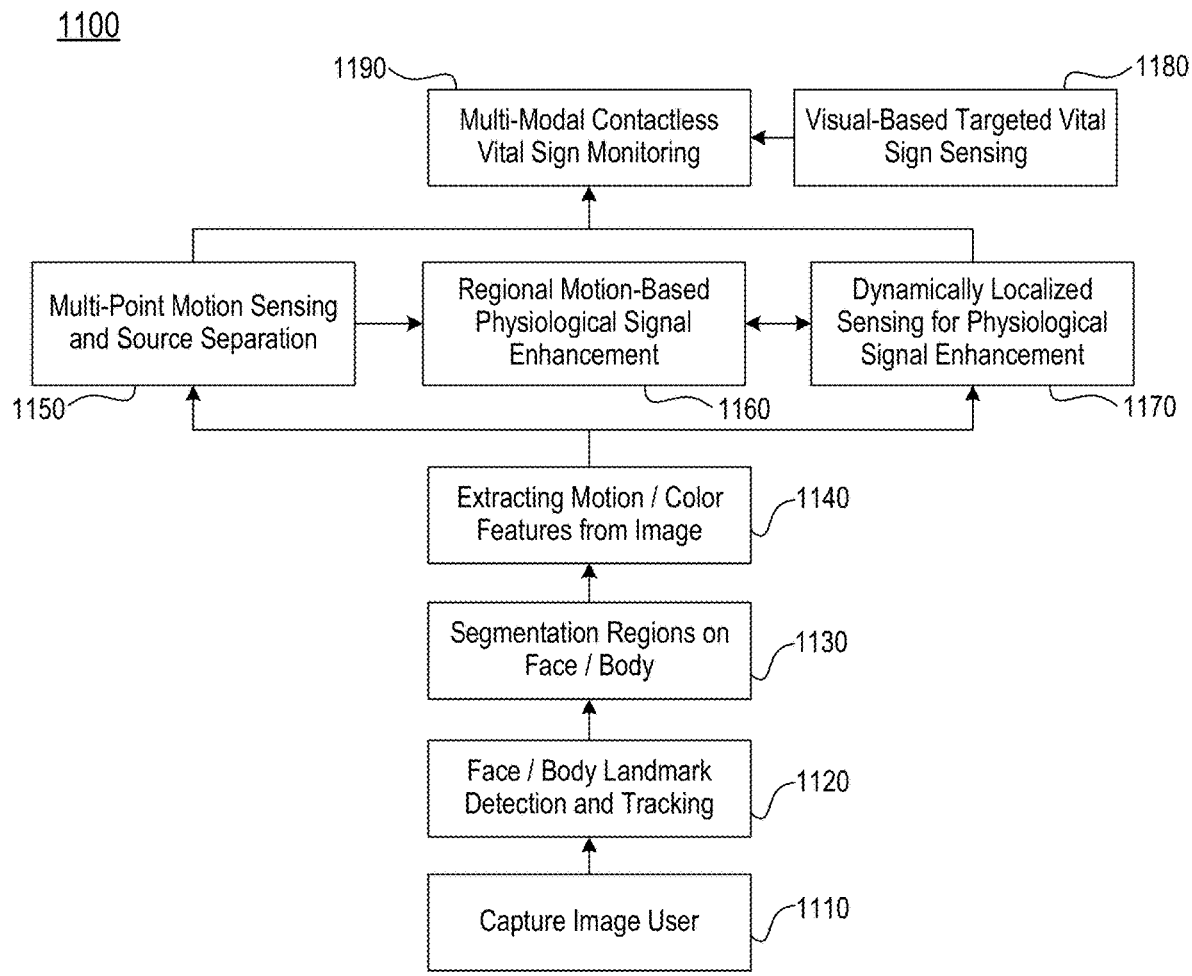
FIG. 11 is a flowchart of an example method using the multimodal, contactless vital sign monitoring system illustrated in FIG. 1, according to an embodiment.

FIG. 11 illustrates an example method 1100 for use with the MCVS system 100. At block 1190, multi-modal (i.e., color and motion) contactless image-based vital sign monitoring is provided using physiological signals from the motion modality and color modality. Beginning with block 1110, a user image is captured consistent with the discussion of the video capture device 190. At block 1120, landmarks on the face and/or body of the subject are detected to be subsequently used for tracking consistent with the discussion of module 106 and portion 122. At block 1130, the face and/or body are dynamically segmented into regions of interest (ROIs)/segments consistent with the discussion of portion 142. At block 1140, motion and color features (modalities) are extracted, in parallel, from selected ROIs/segments/of user's body and/or face within the images consistent with the discussion of portions 124 and 146. The physiological signals from both modalities can be processed separately with respect to their own baseline and variation.

In block 1150 and consistent with the discussion of the motion sensing engine 120, image segments correlated with different parts and landmarks on the body and face are analyzed to extract motion signals and motion type. The pattern of the motion from these different points can be processed to identify the motion type and identify the sources of the motion signal for each ROI/segment. An alternative motion signal for each of the ROIs/segments can be measured using an external device, and signals from both sources can be combined to provide a more accurate signal. The alternative (or complementary) motion signal can be captured by an external device such as multiple motion sensors attached to different regions, depth imaging sensor, or radio-based sensing (e.g., WiFi or UWB). In certain aspects, the visual-based motion signals can be used to target the motion sensing of the external device by correlating the two sources of signal. The motion signals from different points can be analyzed together to evaluate the vital signs, and the evaluation of the vital signs can be fused together with the vital signs evaluated from color to achieve a better accuracy in vital sign determination in block 1190.

In block 1160 and consistent with the discussion of the motion-based enhancement engine 180, regional motion signals correlated with motion artifacts in combination with the physiological signal based on the color features can be used to provide a quantifiable metric of signal quality. Based on the signal quality and motion intensity associated with each ROI/segment, the physiological signals from each region can be weighted in combined.

In block 1170 and consistent with the discussion of the dynamic segmentation and enhancement engine 140, separate analysis of the color features of each dynamically-selected region can provide higher accuracy and more resiliency to ambient light changes and shadows.

In block 1180 and consistent with the discussion of the targeting engine 160, regions to be used for physiological signal extraction can be filtered based on the identity of the user. The user's identity can be determined based on visual features and structure of the tracked face image. A list of regions corresponding to the targeted user can be used to target the physiological signal extraction or vital sign measurement to a specific user for a personalized passive vital sign monitoring. Also, the regions selected in the process of physiological signal extraction can be filtered based on their labels. A prior list of specific parts or regions can be provided to target the physiological signal extraction or vital sign measurement to a specific region for reasons such as privacy concern or more reliable clinical measurement.

Figure 12A:
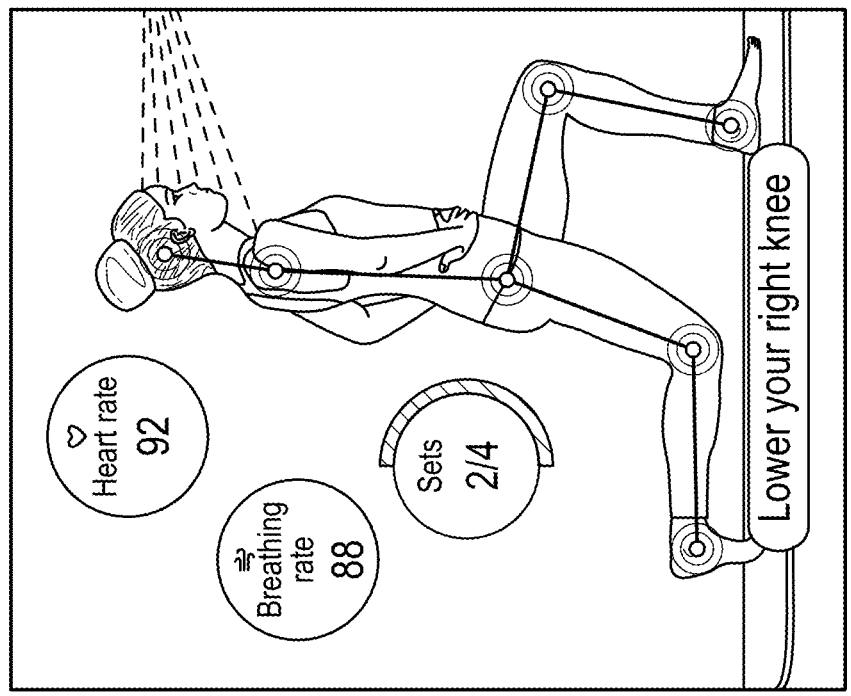
FIGS. 12A-B illustrate, respectively, example usages for the multimodal, contactless vital sign monitoring system, according to an embodiment.
Figure 12B:

FIGS. 12A and 12B represent different use scenarios employing the MCVS system 100. Referring to FIG. 12A, vital signs can be monitored during a fitness activity (e.g., yoga, personal training, home fitness). In this scenario, the MCVS system 100 can be employed to monitor vital signs in real-time using a conventional local device, such as a smart TV, tablet, laptop, or phone camera, with an integrated video capture device 190. For example, the MCVS system 100 can be provided as a selectable app. In certain aspects, with the MCVS system 100 being integrated in the local device, imagery data can be kept private and not remotely circulated.

Using the MCVS system 100, with as little as, for example, 250×250 pixels of exposed skin, physiological signals can be extracted from the imagery. Utilizing the multi-modal aspect (i.e., motion features as well as color features), as little as tens of pixels can be used to track motion from different points. With the substantial resolution of current video capture devices, the MCVS system 100 can determine vital signs from a longer range as well as capture vital signs from multiple individuals within the same field of view of the image capturing device.

Referring to FIG. 12B, vital signs can be monitored during a video call (e.g., telehealth). In this scenario, the MCVS system 100 can be employed to monitor vital signs in real-time using a conventional local device with integrated video capture (not shown), such as a smart TV, tablet, laptop, or phone camera. In certain aspects, with the MCVS system 100 being integrated in the local device, imagery data can be kept private and not circulated remotely.

The benefits of this approach is that real-time and highly-accurate monitoring of multiple vital signs can be facilitated without any specialized hardware. This can lead to fast diagnosis during remote health visits. This MCVS system 100 can also provide passive health monitoring.

Figure 13:
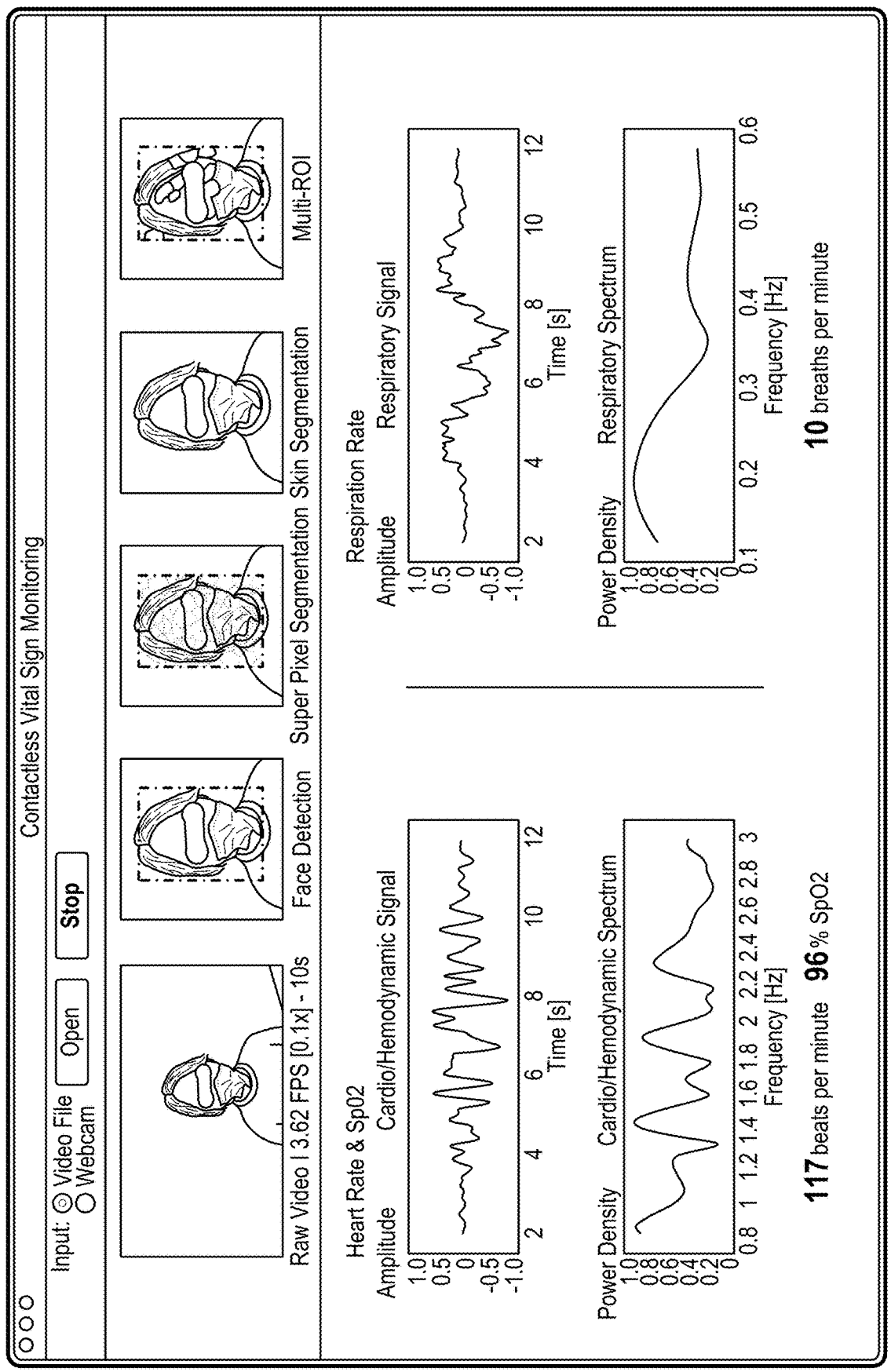
FIG. 13 is an illustrative graphical user interface (GUI) used to test the multimodal, contactless vital sign monitoring system, according to an embodiment.

FIG. 13 is an illustrative graphic user interface (GUI) 1300 used to test the MCVS system 100. The GUI 1300 includes can show raw video, face detection, segmentation, skin segmentation as well as regions of interest. The training of the MCVS system 100 can include using a fitness monitoring chest band to measure reference RR and HR. The algorithms used by the MCVS system 100 to determine the vital signals can be compared with the reference values (i.e., ground truth). This methodology is discussed in more detail with regard to FIGS. 14-16.

Figures 14A, 14B, 14C:
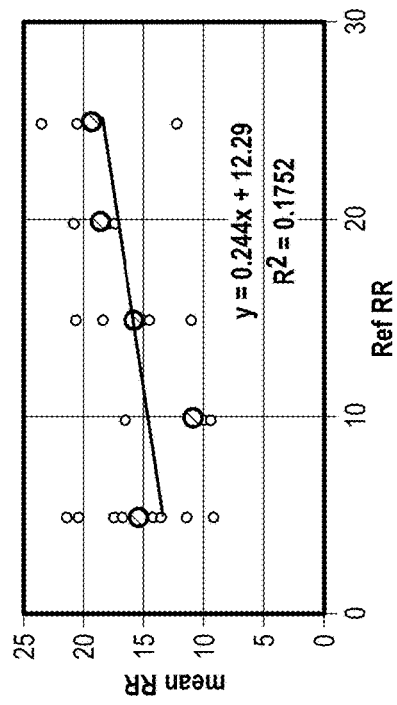
FIGS. 14A-C are tables and graphs illustrating how the mean average error varies depending upon whether all skin is used or whether the fact is dynamically segmented into multiple regions, according to an embodiment.

Referring to FIGS. 14A-C, video was processed to extract RR and HR, and a summary of the results is shown in the illustrated tables. The mean average error (MAE) between the reference values and the estimated HR and RR is shown for each task. In one scenario (all skin), the physiological signals from the whole face were processed together to evaluate the HR and RR. In another scenario, dynamically localized sensing can be employed in which the subject's face is split dynamically into multiple regions. Physiological signals for each region are processed separately and locally with respect to both baseline values and variation. The final HR and RR is calculated by combining values of HR and RR from all the regions. Referring specifically to FIG. 14A, Normal Breathing-15, Normal Breathing-10, and Cool Down refer to a subset of tasks in which subjects are guided to follow certain instructions while their videos and vital signs are being recorded. Specifically, with NormalBreathing-15, the subjects are instructed to look at the camera and normally breathe with a constant rate of 15 breaths per minute for one minute. With Normal Breathing-10, the subjects are instructed to look at the camera and normally breathe with a constant rate of 10 breaths per minute for one minute. With Cool Down, the subjects are instructed to look at the camera and normally breathe at their own pace after a long walk for one minute.

The performance report shows that the localized sensing improves the MAE of HR on average from 7.22 to 4.28 and for RR from 4.67 to 4.38 (considering just the color features). Additionally, the determination coefficient (R-Squared score), which shows correlation between ground truth and estimated RR improved from 0.18 to 0.55.

Referring to FIGS. 15A-B, video was processed to extract RR and HR, and a summary of the results is shown in the illustrated tables. The MAE between the reference values and the estimated RR is shown for each task, and results for 3 different techniques are shown for comparison. A fast Fourier transform (FFT)-based technique provided the best results in this particular example. Using the motion-based enhancement engine 180 (i.e., using additional motion features to improve the quality of the physiological signal), the MAE for RR improved from 4.38 in FIG. 14C to 2.24 in FIG. 15A. Additionally, using the motion-based enhancement engine 180 (i.e., physiological signals from different points are processed separately and combined with weights based on the signal quality such as SNR and motion intensity), the MAE for RR improved from 2.24 to 2.20 bpm on average.

Referring to FIGS. 16A-C, video was processed to extract RR, and a summary of the results is shown in the illustrated tables. The MAE between the reference values and the estimated RR is shown for each task, and the results for 3 different techniques are shown for comparison. The FFT-based technique provided the best result in this particular example.

In one scenario, the physiological signals from multiple regions of the face such as nose, side cheeks and eyebrows were combined to predict the extract the physiological signals including the RR value. In another scenario, the targeting engine 160 was used to filter and select certain regions that have more reliable readings that are less prone to motion artifacts. For example, the eyebrows were removed from the final step and only data from the nose and side cheeks were used for estimation. The results illustrate that removing, for example, the eyebrow data can improve the performance since the eyebrows may move due to other activities such as emotion expression and/or eye blinking. In yet another scenario, the chest area was also selected for respiration since its motion should have the highest correlation with the respiration rate, which was observed in results illustrated in FIG. 16C, which show lower MAE for all the tasks.

Figure 17:
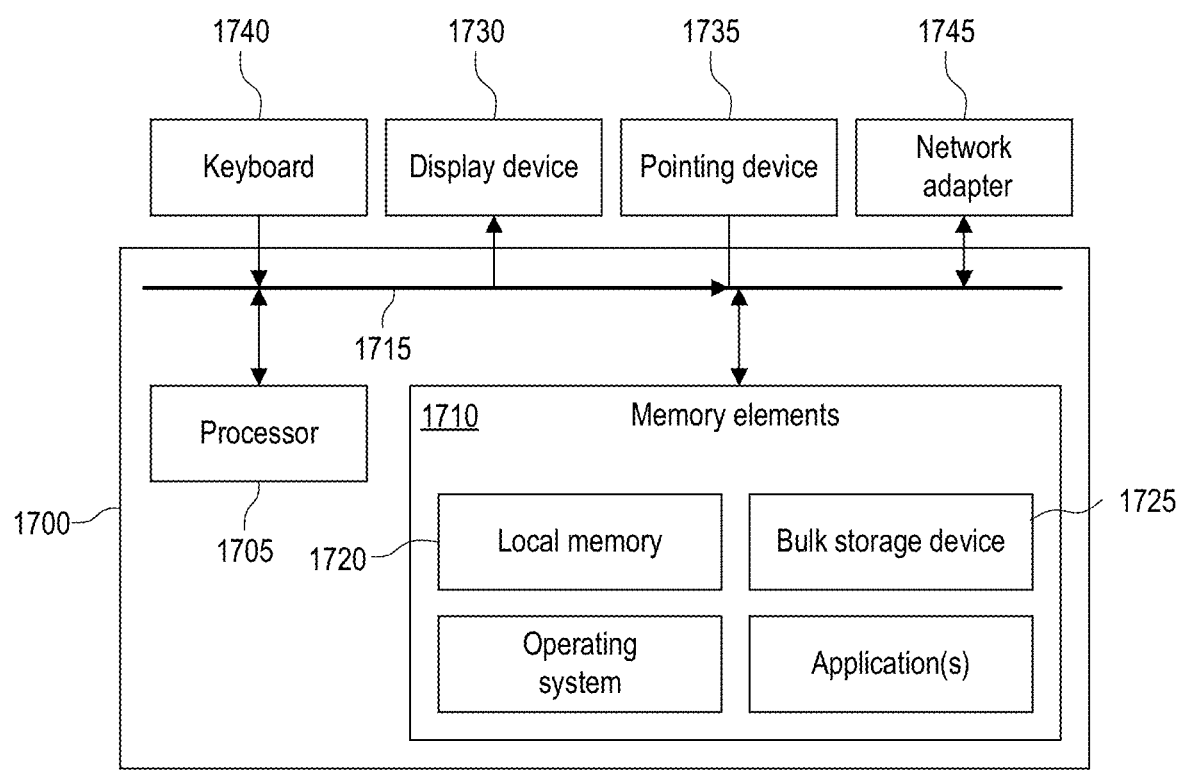
FIG. 17 is a block diagram illustrating an example of a computer hardware system, according to an embodiment.

FIG. 17 is a block diagram illustrating example architecture for a data processing system 1700, such as the MCVS monitoring system 100 illustrated in FIG. 1. The data processing system 1700 can include at least one processor 1705 (e.g., a central processing unit) coupled to memory elements 1710 through a system bus 1715 or other suitable circuitry. As such, the data processing system 1700 can store program code within the memory elements 1710. The processor 1705 can execute the program code accessed from the memory elements 1710 via the system bus 1715. It should be appreciated that the data processing system 1700 can be implemented in the form of any system including a processor and memory that is capable of performing the functions and/or operations described within this specification. For example, the data processing system 1700 can be implemented as a server, a plurality of communicatively linked servers, a workstation, a desktop computer, a mobile computer, a tablet computer, a laptop computer, a netbook computer, a smart phone, a personal digital assistant, a set-top box, a gaming device, a network appliance, and so on.

The memory elements 1710 can include one or more physical memory devices such as, for example, local memory 1720 and one or more bulk storage devices 1725. Local memory 1720 refers to random access memory (RAM) or other non-persistent memory device(s) generally used during actual execution of the program code. The bulk storage device(s) 1725 can be implemented as a hard disk drive (HDD), solid state drive (SSD), or other persistent data storage device. The data processing system 1700 also can include one or more cache memories (not shown) that provide temporary storage of at least some program code in order to reduce the number of times program code must be retrieved from the local memory 1720 and/or bulk storage device 1725 during execution.

Input/output (I/O) devices such as a display 1730, a pointing device 1735 and, optionally, a keyboard 1740 can be coupled to the data processing system 1700. The I/O devices can be coupled to the data processing system 1700 either directly or through intervening I/O controllers. For example, the display 1730 can be coupled to the data processing system 1700 via a graphics processing unit (GPU), which may be a component of the processor 1705 or a discrete device. One or more network adapters 1745 also can be coupled to data processing system 1700 to enable the data processing system 1700 to become coupled to other systems, computer systems, remote printers, and/or remote storage devices through intervening private or public networks. Modems, cable modems, transceivers, and Ethernet cards are examples of different types of network adapters 1745 that can be used with the data processing system 1700.

The terminology used herein is for the purpose of describing particular embodiments only and is not intended to be limiting. Notwithstanding, several definitions that apply throughout this document are expressly defined as follows.

As defined herein, the singular forms "a," "an," and "the" are intended to include the plural forms as well, unless the context clearly indicates otherwise.

As defined herein, the terms "at least one," "one or more," and "and/or," are open-ended expressions that are both conjunctive and disjunctive in operation unless explicitly stated otherwise. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, the term "real time" means a level of processing responsiveness that a user or system senses as sufficiently immediate for a particular process or determination to be made, or that enables the processor to keep up with some external process.

As defined herein, the term "automatically" means without human intervention.

As defined herein, the term "computer readable storage medium" means a storage medium that contains or stores program code for use by or in connection with an instruction execution system, apparatus, or device. As defined herein, a "computer readable storage medium" is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. The different types of memory, as described herein, are examples of a computer readable storage media. A non-exhaustive list of more specific examples of a computer readable storage medium may include: a portable computer diskette, a hard disk, a random-access memory (RAM), a read-only memory (ROM), an erasable programmable read-only memory (EPROM or Flash memory), a static random-access memory (SRAM), a portable compact disc read-only memory (CD-ROM), a digital versatile disk (DVD), a memory stick, a floppy disk, or the like.

As defined herein, "data processing system" means one or more hardware systems configured to process data, each hardware system including at least one processor programmed to initiate operations and memory.

As defined herein, "execute" and "run" comprise a series of actions or events performed by the processor in accordance with one or more machine-readable instructions. "Running" and "executing," as defined herein refer to the active performing of actions or events by the processor. The terms run, running, execute, and executing are used synonymously herein.

As defined herein, the term "if" means "when" or "upon" or "in response to" or "responsive to," depending upon the context. Thus, the phrase "if it is determined" or "if [a stated condition or event] is detected" may be construed to mean "upon determining" or "in response to determining" or "upon detecting [the stated condition or event]" or "in response to detecting [the stated condition or event]" or "responsive to detecting [the stated condition or event]" depending on the context.

As defined herein, the terms "individual" and "user" each refer to a human being.

As defined herein, the term "processor" means at least one hardware circuit (i.e., a hardware processor). The hardware circuit may be configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "responsive to" and similar language as described above, (e.g., "if," "when," or "upon,") mean responding or reacting readily to an action or event. The response or reaction is performed automatically. Thus, if a second action is performed "responsive to" a first action, there is a causal relationship between an occurrence of the first action and an occurrence of the second action. The term "responsive to" indicates the causal relationship.

As defined herein, "server" means a data processing system configured to share services with one or more other data processing systems. Relatedly, "client device" means a data processing system that requests shared services from a server, and with which a user directly interacts. Examples of a client device include, but are not limited to, a workstation, a desktop computer, a computer terminal, a mobile computer, a laptop computer, a netbook computer, a tablet computer, a smart phone, a personal digital assistant, a smart watch, smart glasses, a gaming device, a set-top box, a smart television, and the like. In one or more embodiments, the various user devices described herein may be client devices. Network infrastructure, such as routers, firewalls, switches, access points and the like, are not client devices as the term "client device" is defined herein.

As defined herein, "substantially" means that the recited characteristic, parameter, or value need not be achieved exactly, but that deviations or variations, including for example, tolerances, measurement error, measurement accuracy limitations, and other factors known to those of skill in the art, may occur in amounts that do not preclude the effect the characteristic was intended to provide.

The terms first, second, etc. may be used herein to describe various elements. These elements should not be limited by these terms, as these terms are only used to distinguish one element from another unless stated otherwise or the context clearly indicates otherwise.

A computer program product may include a computer readable storage medium (or media) having computer readable program instructions thereon for causing a processor to carry out aspects of the present disclosure. Within this disclosure, the term "program code" is used interchangeably with the term "computer readable program instructions." Computer readable program instructions described herein may be downloaded to respective computing/processing devices from a computer readable storage medium or to an external computer or external storage device via a network, for example, the Internet, a LAN, a WAN and/or a wireless network. The network may include copper transmission cables, optical transmission fibers, wireless transmission, routers, firewalls, switches, gateway computers and/or edge devices including edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations for the inventive arrangements described herein may be assembler instructions, instruction-set-architecture (ISA) instructions, machine instructions, machine dependent instructions, microcode, firmware instructions, or either source code or object code written in any combination of one or more programming languages, including an object-oriented programming language and/or procedural programming languages. Computer readable program instructions may specify state-setting data. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some cases, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, may be implemented by computer readable program instructions, e.g., program code.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In this way, operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the operations specified in the flowchart and/or block diagram block or blocks.

The computer readable program instructions may also be loaded onto a computer, other programmable data processing apparatus, or other device to cause a series of operations to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various aspects of the inventive arrangements. In this regard, each block in the flowcharts or block diagrams may represent a module, segment, or portion of instructions, which comprises one or more executable instructions for implementing the specified operations. In some alternative implementations, the operations noted in the blocks may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts or carry out combinations of special purpose hardware and computer instructions.

The corresponding structures, materials, acts, and equivalents of all means or step plus function elements that may be found in the claims below are intended to include any structure, material, or act for performing the function in combination with other claimed elements as specifically claimed.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration and are not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art to understand the embodiments disclosed herein. Further, the terms and phrases used within this disclosure are not intended to be limiting, but rather to provide an understandable description of the features described. Any specific structural and functional details described are not to be interpreted as limiting, but merely as a basis for the claims and as a representative basis for teaching one skilled in the art to variously employ the features described in virtually any appropriately detailed structure. Modifications and variations may be apparent to those of ordinary skill in the art without departing from the scope and spirit of the described inventive arrangements. Accordingly, reference should be made to the following claims, rather than to the foregoing disclosure, as indicating the scope of such features and implementations.

What is claimed is:

1. A method of contactless vital sign monitoring, comprising:
   receiving, from a video capture device, images;
   identifying an image of a subject within the images;
   segmenting the image of the subject into a plurality of segments;
   first analyzing the plurality of segments to identify color features of the plurality of segments by establishing, for each of the plurality of segments, a baseline value for each of the plurality of segments, determining, for each of the plurality of segments, a segment value by comparing a detected value to the baseline value, and identifying the color feature based upon a combination of the segment values;
   second analyzing the plurality of segments to identify a motion feature; and
   using a combination of the color features and the motion feature to determine a plurality of vital signs for the subject;
   wherein the first analyzing and the second analyzing are performed in parallel; and
   wherein the second analyzing includes:
      identifying a plurality of landmarks of the subject visible in the image of the subject;
      identifying, for each of the plurality of landmarks, a movement over a plurality of images of the subject;
      identifying the motion feature based upon a combination of the movements of the landmarks;
      distinguishing between a motion artifact not associated with the plurality of vital signs and physiological activity data that is associated with the plurality of vital signs, wherein the motion artifact includes head movement detected, at least in part, using optical flow to detect the movements over the plurality of images; and
      excluding, from the identifying the motion feature, the motion artifact.

2. The method of claim 1, wherein
   the plurality of segments are classified into a first classification and a second classification,
   the plurality of segments are filtered based upon the first classification and the second classification, and
   the establishing the baseline value and the determining the segment value are performed only for the plurality of segments classified into the first classification.

3. The method of claim 1, wherein the optical flow detects distances of the movements of the landmarks over the plurality of images.

4. The method of claim 3, wherein the landmarks include at least one of eyes or a nose of a face of the subject.

5. The method of claim 1, wherein
   a plurality of subjects are found within the images, and
   a particular one of the plurality of subjects is selected to be the subject.

6. The method of claim 1, wherein
   the color feature and the motion feature are weighed based upon signal quality and motion intensity.

7. The method of claim 1, wherein
   the plurality of vital signs include one or more of heart rate, respiration rate, oxygen saturation, heart rate variability, or atrial fibrillation.

8. A multimodal, contactless vital sign monitoring system, comprising:
   a computer hardware system configured to perform:
      receiving, from a video capture device, images;
      identifying an image of a subject within the images;
      segmenting the image of the subject into a plurality of segments;
      first analyzing the plurality of segments to identify a color feature by establishing, for each of the plurality of segments, a baseline value for each of the plurality of segments, determining, for each of the plurality of segments, a segment value by comparing a detected value to the baseline value, and identifying the color feature based upon a combination of the segment values;
      second analyzing the plurality of segments to identify a motion feature; and
      using a combination of the color feature and the motion feature to determine a plurality of vital signs for the subject;
      wherein the first analyzing and the second analyzing are performed in parallel; and
      wherein the second analyzing includes:
         identifying a plurality of landmarks of the subject visible in the image of the subject;
         identifying, for each of the plurality of landmarks, a movement over a plurality of images of the subject;
         identifying the motion feature based upon a combination of the movements of the landmarks;
         distinguishing between a motion artifact not associated with the plurality of vital signs and physiological activity data that is associated with the plurality of vital signs, wherein the motion artifact includes head movement detected, at least in part, using optical flow to detect the movements over the plurality of images; and
         excluding, from the identifying the motion feature, the motion artifact.

9. The system of claim 8, wherein
   the plurality of segments are classified into a first classification and a second classification,
   the plurality of segments are filtered based upon the first classification and the second classification, and the establishing the baseline value and the determining establishing the segment value are performed only for the plurality of segments classified into the first classification.

10. The system of claim 8, wherein the optical flow detects distances of the movements of the landmarks over the plurality of images.

11. The system of claim 10, wherein the landmarks include at least one of eyes or a nose of a face of the subject.

12. The system of claim 8, wherein
a plurality of subjects are found within the images, and
a particular one of the plurality of subjects is selected to be the subject.

13. The system of claim 8, wherein
the color feature and the motion feature are weighed based upon signal quality and motion intensity.

14. The system of claim 8, wherein
the plurality of vital signs include one or more of heart rate, respiration rate, oxygen saturation, heart rate variability, or atrial fibrillation.

15. A computer program product, comprising:
one or more computer readable storage mediums and program instructions collectively stored on the one or more computer readable storage mediums,
the program instructions, which when executed by a multimodal, contactless vital sign monitoring system, causes the multimodal, contactless vital sign monitoring system to perform:
  receiving, from a video capture device, images;
  identifying an image of a subject within the images;
  segmenting the image of the subject into a plurality of segments;
  first analyzing the plurality of segments to identify a color feature by establishing, for each of the plurality of segments, a baseline value for each of the plurality of segments, determining, for each of the plurality of segments, a segment value by comparing a detected value to the baseline value, and identifying the color feature based upon a combination of the segment values;
  second analyzing the plurality of segments to identify a motion feature; and
  using a combination of the color feature and the motion feature to determine a plurality of vital signs for the subject;
wherein the first analyzing and the second analyzing are performed in parallel; and
wherein the second analyzing includes:
  identifying a plurality of landmarks of the subject visible in the image of the subject;
  identifying, for each of the plurality of landmarks, a movement over a plurality of images of the subject;
  identifying the motion feature based upon a combination of the movements of the landmarks;
  distinguishing between a motion artifact not associated with the plurality of vital signs and physiological activity data that is associated with the plurality of vital signs, wherein the motion artifact includes head movement detected, at least in part, using optical flow to detect the movements over the plurality of images; and
  excluding, from the identifying the motion feature, the motion artifact.

16. The computer program product of claim 15, wherein the plurality of vital signs include one or more of heart rate, respiration rate, oxygen saturation, heart rate variability, or atrial fibrillation.

17. The computer program product of claim 15, wherein the plurality of segments are classified into a first classification and a second classification,
the plurality of segments are filtered based upon the first classification and the second classification, and
the establishing the baseline value and establishing the segment value are performed only for the plurality of segments classified into the first classification.

18. The computer program product of claim 15, wherein the optical flow detects a distance of the movements of the landmarks over the plurality of images.

* * * * *